United States Patent
Alt et al.

(10) Patent No.: US 10,905,722 B2
(45) Date of Patent: *Feb. 2, 2021

(54) INDUCED PACEMAKER AND PURKINJE CELLS FROM ADULT STEM CELLS

(71) Applicants: InGeneron, Inc, Houston, TX (US); Alliance of Cardiovascular Researchers, New Orleans, LA (US)

(72) Inventors: Eckhard Alt, Houston, TX (US); Tahereh Karimi, Houston, TX (US)

(73) Assignees: INGENERON INC., Houston, TX (US); ALLIANCE OF CARDIOVASCULAR RESEARCHERS, New Orleans, LA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/914,782

(22) Filed: Mar. 7, 2018

(65) Prior Publication Data

US 2018/0264046 A1    Sep. 20, 2018

Related U.S. Application Data

(62) Division of application No. 14/980,274, filed on Dec. 28, 2015, now Pat. No. 9,913,865.

(51) Int. Cl.
| | | |
|---|---|---|
| *C12N 5/00* | (2006.01) |
| *A61K 35/34* | (2015.01) |
| *C12N 5/077* | (2010.01) |
| *C12N 5/079* | (2010.01) |
| *A61K 35/30* | (2015.01) |

(52) U.S. Cl.
CPC .............. *A61K 35/34* (2013.01); *A61K 35/30* (2013.01); *C12N 5/0618* (2013.01); *C12N 5/0657* (2013.01); *C12N 2501/60* (2013.01); *C12N 2501/998* (2013.01); *C12N 2506/08* (2013.01); *C12N 2506/1384* (2013.01); *C12N 2510/00* (2013.01)

(58) Field of Classification Search
None
See application file for complete search history.

(56) References Cited

U.S. PATENT DOCUMENTS

| | | |
|---|---|---|
| 2014/0273207 A1 | 9/2014 | Chan et al. |
| 2014/0308746 A1 | 10/2014 | Rossi et al. |
| 2015/0164957 A1 | 6/2015 | Arnolds et al. |
| 2015/0359845 A1 | 12/2015 | Marban et al. |

FOREIGN PATENT DOCUMENTS

| | | |
|---|---|---|
| EP | 16882595.8 | 7/2019 |
| WO | WO2017117276 | 7/2017 |

OTHER PUBLICATIONS

Unudurthi, S. et al., 2014, Frontiers in Phys., vol. 5, 7 pages.*
Hashem et al. Genetic isolation of stem cell-derived pacemaker-nodal cardiac myocytes. Mol. Cell. Biochem. Nov. 2013, vol. 383 No. 1-2, pp. 161-171.
V. Vedantham, New Approaches to Biological Pacemakers: Links to Sinoatrial Node Development, Trends in Molecular Medicine, vol. 21, No. 12, pp. 749-761, XP029329385, ISSN: 1471-4914, DOI: 10.1016/J.MOLMED 2015.10.002.
D. Spater et al., How to make a cardiomyocyte, Development, vol. 141, No. 23, Nov. 18, 2014, pp. 4418-4431, XP055421693, GB ISSN: 0950-1991, DOI: 101242/dev.091538.
Adriana Blazeski et al., Electrophysiological and contractile function of cardiomyocytes derived from human embryonic stem cells, Progress in Biophysics and Molecular Biology, vol. 110, No. 2-3, Oct. 1, 2012, pp. 178-195, XP055490205, Amsterdam, NL ISSN: 0079-6107, DOI: 10.1016/j.pbiomolbio.2012.07.012.

* cited by examiner

*Primary Examiner* — Michael D Burkhart
(74) *Attorney, Agent, or Firm* — Boulware & Valoir

(57) ABSTRACT

Adult stem cells are reprogrammed to form pacemaker cells and Purkinje cells through the sequential activation of SHOX2>TBX5>HCN2. These Purkinje cells spontaneously surround and connect with the larger pacemaker cells, thus forming an induced sinoatrial body that produces funny current and can make cardiovascular tissues beat in a manner similar to a natural sinoatrial node.

3 Claims, 17 Drawing Sheets
Specification includes a Sequence Listing.

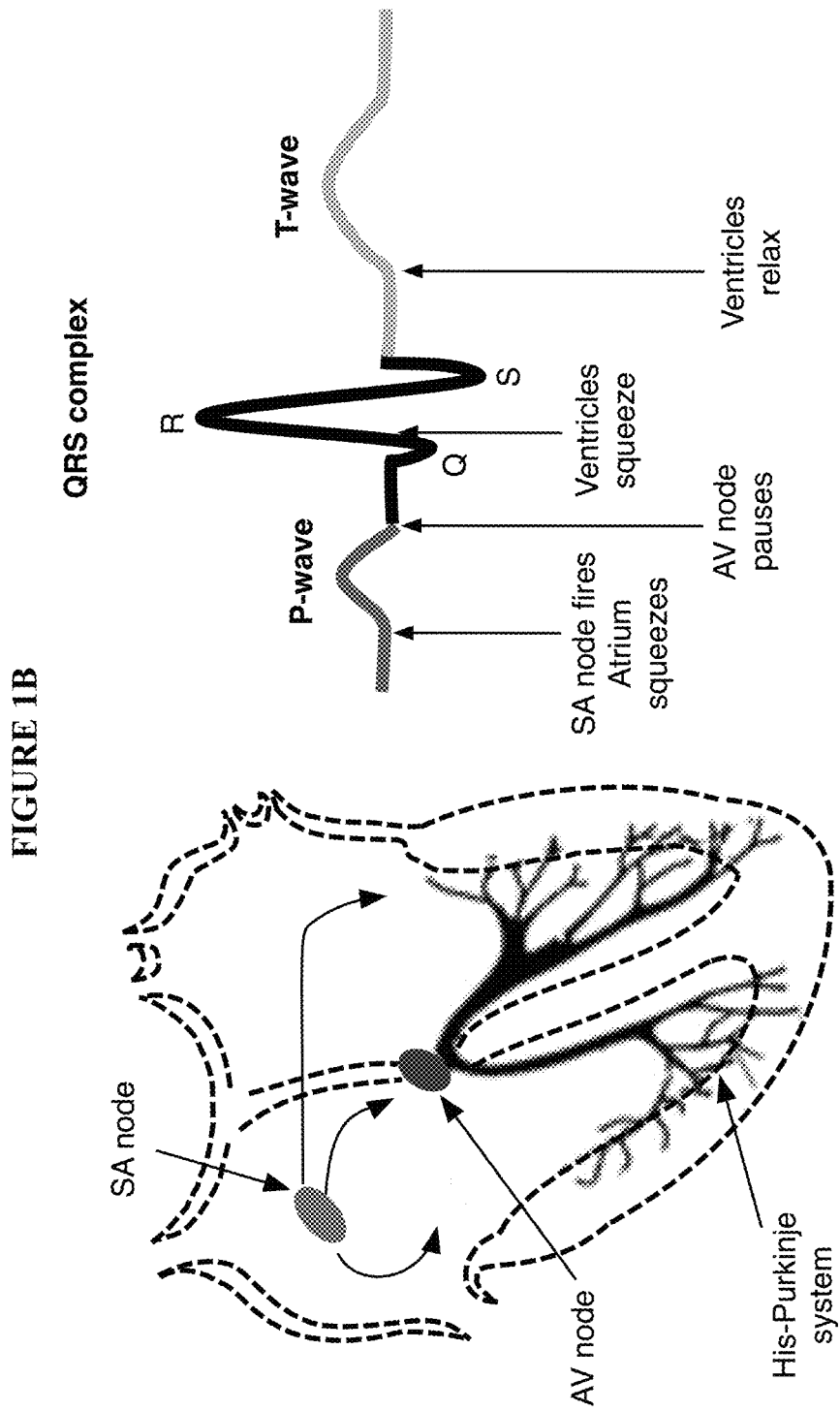

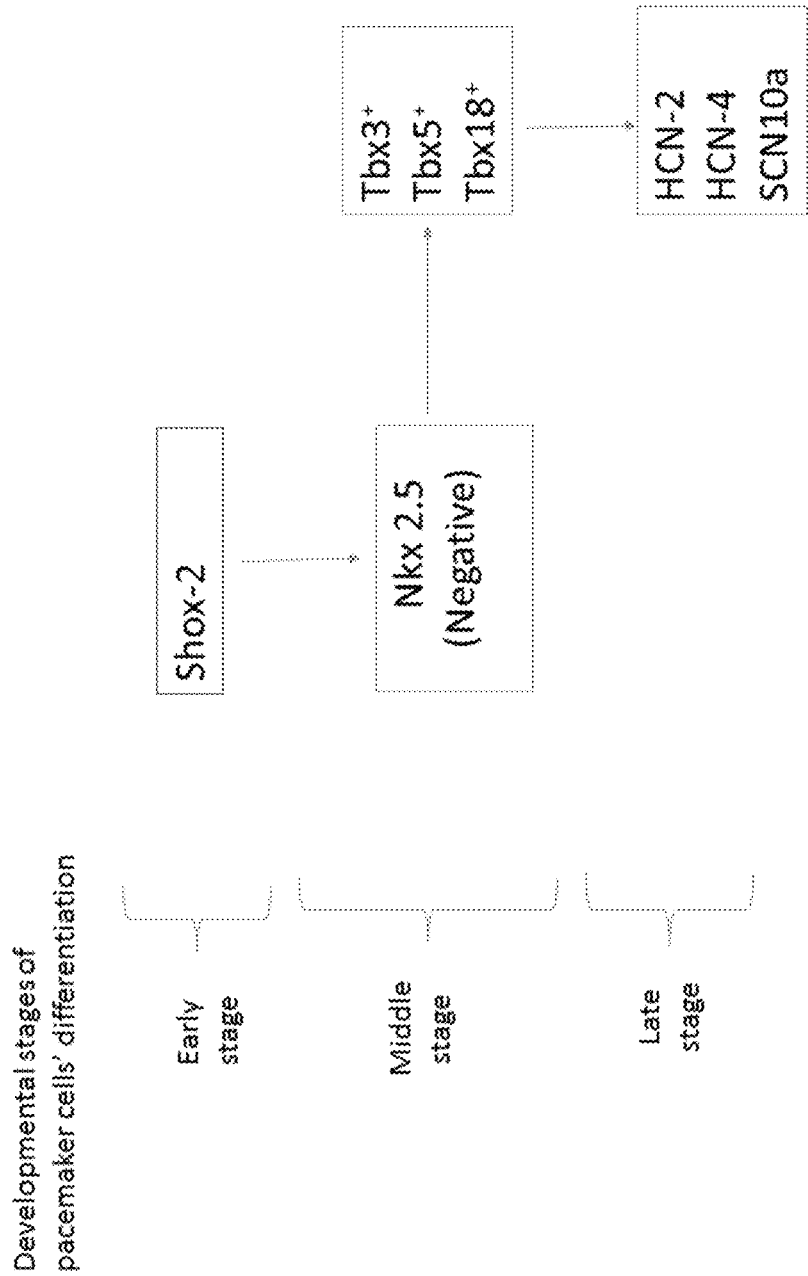

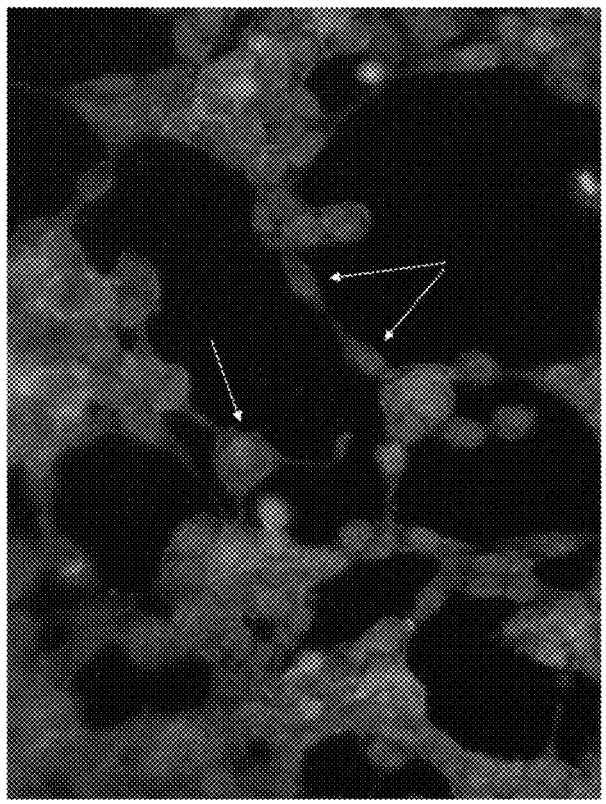
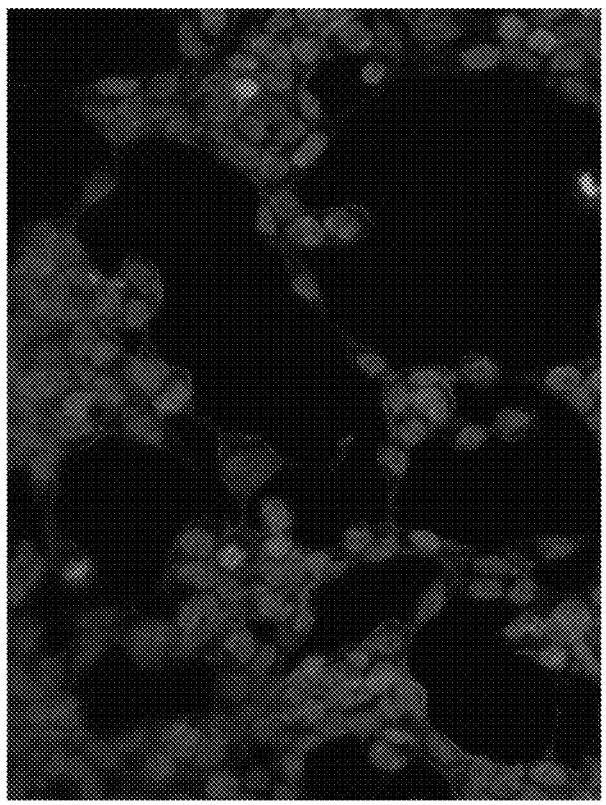
FIGURE 11

FIGURE 13

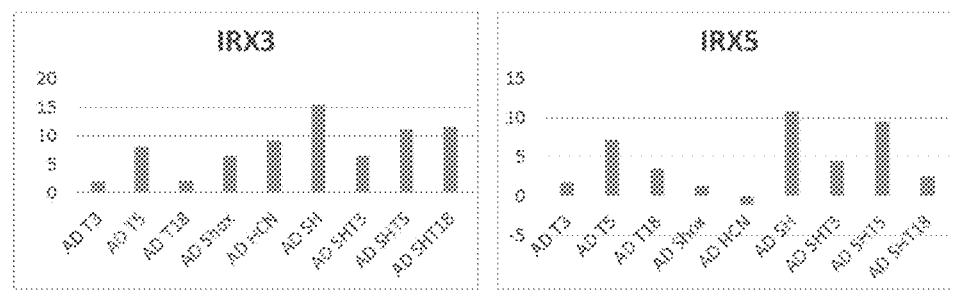
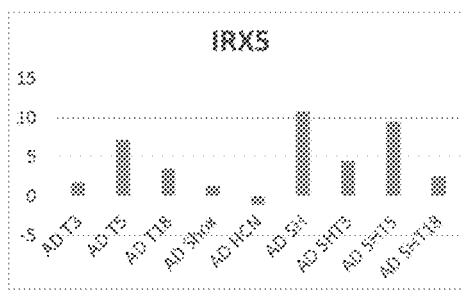
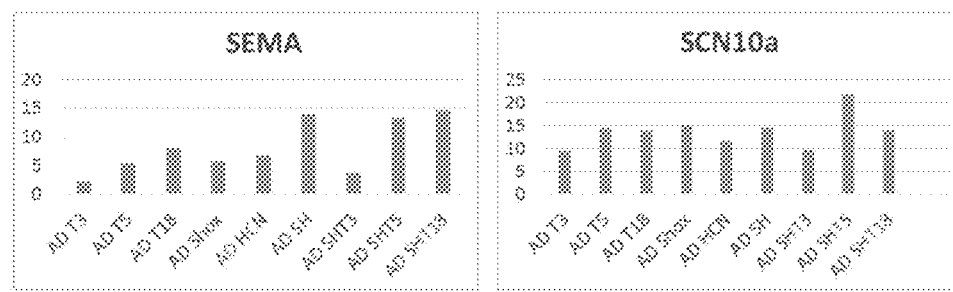
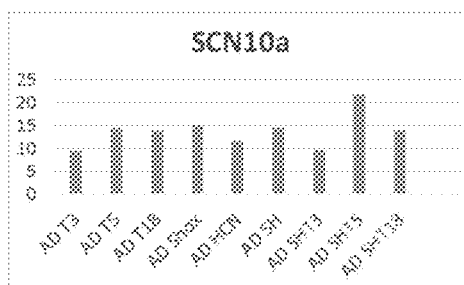
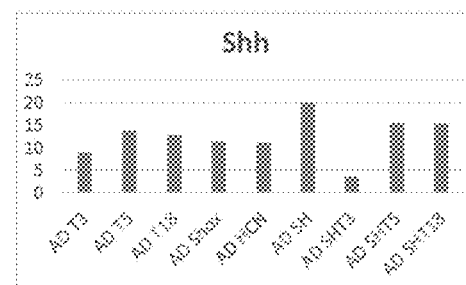

| |
|---|
| AD T3: ADSCs transfected with TBX3 alone, |
| AD T5: ADSCs transfected with TBX5 alone, |
| AD T18: ADSCs transfected with TBX18 alone, |
| AD SHOX: ADSCs transfected with SHOX2 alone, |
| AD HCN: ADSCs transfected with HCN2 alone, |
| AD SH: ADSCs transfected with SHOX2 and HCN2, |
| AD SHT3: ADSCs transfected with SHOX2, TBX3 and HCN2, |
| AD SHT5: ADSCs transfected with SHOX2, TBX5 and HCN2, |
| AD SHT18: ADSCs transfected with SHOX2, TBX18 and HCN2 |

FIGURE 14: RNA EXPRSSSION LEVELS CONT.

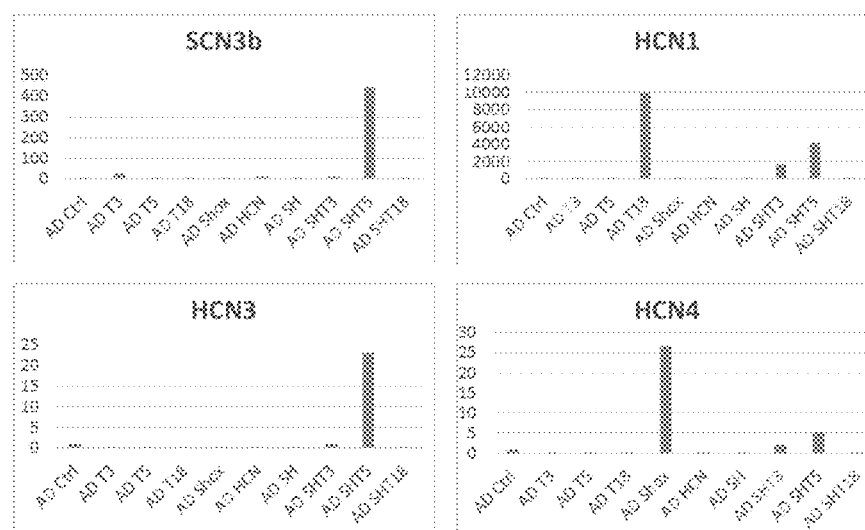

| AD T3: ADSCs transfected with TBX3 alone, |
| AD T5: ADSCs transfected with TBX5 alone, |
| AD T18: ADSCs transfected with TBX18 alone, |
| AD SHOX: ADSCs transfected with SHOX2 alone, |
| AD HCN: ADSCs transfected with HCN2 alone, |
| AD SH: ADSCs transfected with SHOX2 and HCN2, |
| AD SHT3: ADSCs transfected with SHOX2, TBX3 and HCN2, |
| AD SHT5: ADSCs transfected with SHOX2, TBX5 and HCN2, |
| AD SHT18: ADSCs transfected with SHOX2, TBX18 and HCN2 |

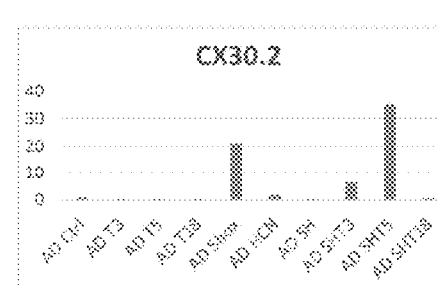

INDUCED PACEMAKER AND PURKINJE CELLS FROM ADULT STEM CELLS

PRIOR RELATED APPLICATIONS

Not applicable.

FIELD OF THE DISCLOSURE

This invention relates to methods for the generation of non contractile, electrically active induced cardiomyocyte cells for use in treatment of arrhythmias, as well as the induced creation and formation of cells for enhanced electrical activity of the heart such as sinus or sinoatrial node cells and Purkinje cells of the heart thereby produced and used for same.

BACKGROUND OF THE DISCLOSURE

The heart (FIG. 1A) is the muscular organ that pumps blood through the blood vessels of the circulatory system. In a healthy mammalian heart, composed of right and left atrium and right and left ventricles, blood flows only one way through the heart because the heart valves prevent backflow. The heart is enclosed in a protective sac, the pericardium, which also contains a small amount of fluid. The wall of the heart is made up of three layers: epicardium, myocardium, and endocardium.

The sinoatrial node (often abbreviated SA node or SAN; also commonly called the sinus node and less commonly the sinuatrial node) is the pacemaker of the heart and is responsible for the initiation of the heartbeat. It is located at the junction of the vena cava superior and the atrium, and measures about 5 mm by 2 cm. It spontaneously generates an electrical impulse, which after conducting throughout the heart, causes the heart to contract. Although the electrical impulses are generated spontaneously, the rate of the impulses (and therefore the heart rate) is modified by the nerves innervating the sinoatrial node, located in the right atrium (upper chamber) of the heart.

The atrioventricular (AV) node is a part of the electrical conduction system of the heart that coordinates the contractions of the heart chambers. It electrically connects atrial and ventricular chambers (FIG. 1B). The AV node is an area of specialized tissue between the atria and the ventricles of the heart, specifically in the posteoinferior region of the interatrial septum near the opening of the coronary sinus, which conducts the normal electrical impulse from the atria to the ventricles. The AV node is quite compact (~1×3×5 mm). It is located at the center of Koch's triangle—a triangle enclosed by the septal leaflet of the tricuspid valve, the coronary sinus, and the membraneous part of the interatrial septum.

The distal portion of the AV node is known as the Bundle of His. The Bundle of His splits into two branches in the interventricular septum, the left bundle branch and the right bundle branch. The left bundle branch activates the left ventricle, while the right bundle branch activates the right ventricle. The two bundle branches taper out to produce numerous Purkinje fibers, which stimulate individual groups of myocardial cells to contract.

Funny current (or funny channel, or If or IKf, or pacemaker current) refers to a specific current in the heart. First described in the late 1970s in Purkinje fibers and sinoatrial myocytes, the cardiac pacemaker "funny" current has been extensively characterized and its role in cardiac pacemaking has been investigated.

The funny current is highly expressed in spontaneously active cardiac regions, such as the sinoatrial node, the atrioventricular node and the Purkinje fibers of conduction tissue. The funny current is a mixed sodium-potassium current that activates upon hyperpolarization at voltages in the diastolic range (normally from −60/−70 mV to −40 mV). When at the end of a sinoatrial action potential, the membrane repolarizes below the If threshold (about −40/−50 mV), the funny current is activated and supplies inward current, which is responsible for starting the diastolic depolarization phase (DD). With this mechanism, the funny current controls the rate of spontaneous activity of sinoatrial myocytes and thus the cardiac rate.

The molecular determinants of the pacemaker current belong to the Hyperpolarization-activated Cyclic Nucleotide-gated channels family (HCN) of which 4 isoforms (HCN1-4) are known to date. Based on their sequence, HCN channels are classified as members of the superfamily of voltage-gated K+(Kv) and cyclic nucleotide-gated (CNG) ion channels.

In simple terms, the electrical signals that control the heartbeat can be described as follows. The electrical impulse starts in the SA node. The electrical activity spreads through the walls of the atria and causes them to contract. This forces blood into the ventricles. The AV node acts like a gate that slows the electrical signal before it enters the ventricles. This delay gives the atria time to contract before the ventricles do. After this delay, the stimulus diverges and is conducted through the left and right bundle of His to the respective Purkinje fibers for each side of the heart, as well as to the endocardium at the apex of the heart, then finally to the ventricular epicardium. The His-Purkinje Network of fibers sends the impulse to the muscular walls of the ventricles and causes them to contract. This forces blood out of the heart to the lungs and body. The SA node fires another impulse and the cycle begins again.

Many things can go wrong with the heart resulting in irregular beating. Sick sinus syndrome—also known as sinus node disease or sinus node dysfunction—is the name for a group of heart rhythm problems (arrhythmias) in which the sinus node—the heart's natural pacemaker—doesn't work properly.

An artificial pacemaker is a medical device that uses electrical impulses, delivered by electrodes depolarizing the heart muscles, to regulate the beating of the heart. The primary purpose of the artificial pacemaker is to maintain an adequate heart rate, either because the heart's natural pacemaker is not fast enough, or because there is a block in the heart's electrical conduction system. Modern pacemakers are externally programmable and allow a cardiologist to select the optimum pacing modes for individual patients. Some combine a pacemaker and defibrillator in a single implantable device. Others have multiple electrodes stimulating differing positions within the heart to improve synchronization of the higher (atria) and the lower chambers (ventricles) of the heart.

Although artificial pacemakers have saved many lives, they are not a perfect solution. In particular, they are not hormone responsive, are subject to mechanical and/or electrical failure, need battery replacement and can be disrupted in strong magnetic fields or in therapeutic radiation settings. Further, infection is always a hazard, as is pacemaker-mediated tachycardia, suboptimal atrioventricular (AV) synchrony, and several other types of pacemaker induced dysrhythmias. Therefore, there are ongoing efforts to develop a more natural pacemaker.

Biological pacemakers, generally intended as cell substrates able to induce spontaneous activity in silent tissue, represent a potential tool to overcome the limitations of electronic pacemakers. Efforts to develop natural pacemakers for use in place of artificial pacemakers have generally taken one of two approaches.

One approach is to convert beating myocardium into pacemaker cells in situ via genetic manipulations (i.e., direct reprogramming). In this regard, the early key transcription factor TBX3 provided promising results, but led to cells with incomplete pacemaker characteristics.

Another approach is to use embryonic or induced pluripotent stem cells (so called IPS cells) that have been programmed to form pacemaker cells, and then replace or supplement AV cells with these newly programmed AV-like cells.

In a study, Jung et al. attempted to generate pacemaker cells by up-regulation of TBX3 in induced pluripotent stem cells (iPSCs). Hashem et al. (2013) indicated that SHOX2 regulates the pacemaker gene program in embryoid bodies. Bakker et al. (2012) attempted to reprogram terminally differentiated cardiomyocytes towards pacemaker cells by upregulation of TBX3. In another study Kapoor et al. (2013) attempted to generate pacemaker cells by overexpression of TBX18 in adult cardiomyocytes. Hu et al. (2014) tried to convert cardiomyocytes into pacemaker cells by upregulation of Tbx18.

Despite several attempts in the past to generate cardiac pacemaker cells, there are up to now no correctly functional biological pacemaker cells available for clinical application derived from undifferentiated adult autologous stem cells. It only has been shown before that cells like embryonic cells or IPS cells could be induced by manipulation of certain genes to obtain some features that are present in pacemaker or in other cells of the cardiac conduction system. The expression of a single transcription factor alone was not able to switch on the complete respective regulatory differentiation pathway towards pacemaker or Purkinje cells. Attempts to generate pacemaker cells in the past failed to mimic the appropriate physiological functionality and morphological properties of natural cardiac pacemaker cells.

The work described herein, takes this research to a new and higher state: The induction of differentiation of adult, unmodified, fresh uncultured cells (herein also called regenerative cells) from the patient's own tissue into non-contractile cardiomyocyte cells with morphological and functional structure and features of natural pacemakers and Purkinje cells has not been achieved before.

SUMMARY OF DISCLOSURE

Induced pacemaker cells, Purkinje cells and the sinoatrial bodies produced by their association are described herein, as well as method of making and using same.

Using both lentiviral and mRNA based transfection approaches, adipose derived stem cells (ADSCs) have been reprogrammed towards cardiac pacemaker cells by the respective subsequent application of a combination of transcription factors including SHOX2, TBX3, TBX5, TBX18 and HCN2.

SHOX2 is a negative regulator of NKX 2.5 in the SA node, which inhibits the contractile cardiomyocytes differentiation pathway, but specifically directs the primitive respectively progenitor cells toward the non-contractile cardiomyocyte pacemaker cell lineage by up-regulation of the pacemaker differentiation pathway. TBX3, TBX5 and TBX18 are the main transcription factors regulating the differentiation of primitive mesodermal derived stem cells towards the pacemaker cell lineage and the formation of SAN.

Mature pacemaker cells at the late stage of tissue development differ from common cardiomyocytes for the presence of spontaneous depolarization processes, which are caused by an unstable phase 4 potential that progressively reduces the membrane potential during the diastolic phase of the cardiac cycle. When the reduction reaches a critical threshold value, the sodium channels open and the action potential induces. The spontaneous diastolic depolarization of pacemaker cells is due to the hyperpolarization-activated cyclic nucleotide-gated (HCN) channel genes, which code for specific proteins, providing the presence of an inward current named If or funny current. Expression of HCN2 is believed to be important for appropriate physiological functionality of pacemaker cells, but its possible that other HCN genes can replace or supplement HCN2.

The invention is described in more detail below.

Pacemaker Reprogramming Genes

SHOX2 (UniProt 060902), aka SHORT STATURE HOMEOBOX 2 or SHOT, was identified as gene related to the human short stature homeobox gene (SHOX; 312865) and the mouse og12 gene. The original discoverers showed that SHOX2 shows a much higher degree of homology to og12 than does SHOX. Two different isoforms were isolated, called SHOTa and SHOTb therein, which have identical homeodomains and share a C-terminal 14-amino acid residue motif characteristic for craniofacially expressed homeodomain proteins. The differences between SHOTa and SHOTb were within the N-termini and an alternatively spliced exon in the C termini. In situ hybridization of og12 on sections from staged mouse embryos detected highly restricted transcripts in the developmental sinus venosus (aorta), female genitalia, diencephalon, mes- and myelencephalon, nasal capsula, palate, eyelid, and limbs. Isoform 1 is 330 amino acids and contains a homeobox DNA-binding domain.

TBX5 (UniProt Q99593), aka T-BOX-5, spans 9 exons and more than 47 kb and mutations in this protein are responsible for Holt-Oram syndrome, a developmental disorder affecting the heart and limbs. Researchers found that P19CL6 cell lines overexpressing wildtype TBX5 started to beat earlier and expressed cardiac-specific genes more abundantly than did parental P19CL6 cells, whereas cell lines expressing the G80R mutation (601620.0004), which causes substantial cardiac defects with minor skeletal abnormalities in HOS, did not differentiate into beating cardiomyocytes. Contrarily, the R237Q mutation (601620.0003), which causes upper limb malformations without cardiac abnormalities, activated the Nppa promoter to an extent similar to that of wildtype TBX5. Isoform 1 is 558 amino acids.

In place of or in addition to TBX5, TBX3 (UniProt O15119) can be used in the methods described herein. TBX3, aka T-BOX-3, identified along with TBX5 in studying linkage to Holt-Oram syndrome. There are alternatively transcribed TBX3 transcripts, including 1 that interrupts the T-box. The complete open reading frame of the TBX3 gene encodes a predicted 723-amino acid protein. Comparison of other T-box genes to TBX3 indicated regions of substantial homology outside the DNA-binding domain.

In addition to being involved in limb pattern formation, TBX3 is involved in pacemaker development. Using genetic lineage analysis, knockout studies, and explant assays, it was found that TBX18 (OMIM 604613) was required to establish the large head structure of the mouse sinoatrial node from mesenchymal precursors. Subsequently, TBX3 induced expression of pacemaker genes for pacemaker function. It has also been used to improve the quality of induced pluripotent stem (iPS) cells.

TBX18 (UniProt O95935) can also be used in the methods described herein. TBX18 or T-BOX-18 acts as transcriptional repressor involved in developmental processes of a variety of tissues and organs, including the heart and coronary vessels, the ureter and the vertebral column. It is required for embryonic development of the sino atrial node (SAN) head area. As typical in this family, there are several exons (8), at least 4 transcripts, and the full length protein is 607 aa.

HCN2 (UniProt Q9UL51), aka HYPERPOLARIZATION-ACTIVATED CYCLIC NUCLEOTIDE-GATED POTASSIUM CHANNEL 2 and BRAIN CYCLIC-NUCLEOTIDE GATED 2; BCNG2, is believed to be one of the pacemaker ion channels. The HCN2 gene contains 8 exons spanning about 27 kb, and like all channels it is quite large at 889 amino acids, having at least 6 transmembrane domains. This hyperpolarization-activated ion channel exhibits weak selectivity for potassium over sodium ions, and contributes to the native (funny) pacemaker currents in heart (If).

Method Overview

Generally speaking, we use adult uncultured and initially unmodified adipose tissue derived regenerative cells that include very early pluripotent stem cells and progenitor cells. The use of autologous cells from the same patient that requires repair of an arrhythmia of his or her heart, both bradycardic or tachycardic, is preferred.

These cells are transfected with sequential expression vectors encoding SHOX2, TBX5 and HCN2, or SHOX2, TBX3, TBX5, TBX18 and HCN2 such that each of the genes is transcribed in a sequential and organized mode, leading to production of functional proteins.

The use of adipose tissue derived stem cells is exemplary only and any suitable regenerative cell preparation can be used. Regenerative cells preparations for example include cells from bone narrow, umbilical cord tissue, umbilical cord blood, placenta, blood or any other tissue of the body such as roots of hair or omental fat containing blood vessels and thereby containing the early stem cells that are able to be induced to generate pacemaker cells with the method described in this application. This list of possible cells is only exemplary and not exhaustive.

In our experience, the proteins should be sequentially introduced into the cell in a particular sequence order and amount (FIG. 2). Attempting to transfect all genes at once killed a majority of cells. However, with better introduction systems, it may be possible that the cells will not be as shocked and may survive. Order of activation, however, is expected to continue to be important, as is the level of expression.

The vectors used herein were lentiviral vectors, however, this is exemplary only and any expression vector can be used. Alternatively, RNA could be used or even intact functional proteins.

DNA, RNA and protein can be introduced into the cells in a variety of ways, including e.g., microinjection, electroporation, and lipid-mediated transfection. RNA can also be deliver to cells using e.g., tat fusion using e.g., the HIV-1-tat protein. Tat has successfully been used for protein delivery. For example, a tetramethylrhodamine-labeled dimer of the cell-penetrating peptide TAT, dfTAT, penetrates live cells by escaping from endosomes with high efficiency. Other cell-penetrating peptides (CPPs) are known, and indeed intact proteins can be delivered using CPPs as fusion proteins, as well as by non-covalent CPP/protein complexes.

At the current time retroviruses are preferred for gene therapies (retroviral and lentiviral) and have now been used in more than 350 gene-therapy studies. Retroviral vectors are particularly suited for gene-correction of cells due to long-term and stable expression of the transferred transgene(s), and also because little effort is required for their cloning and production. However, it is anticipated that next generation vectors will continue to be developed that can be equally used for the purpose of induction of pacemaker cells.

Furthermore, with the advent of genome engineering techniques (such as CRISP/CAS, and the like), it may also be possible in the future to selectively activate the needed proteins via genome engineering, rather than by cell delivery of DNA, RNA, or protein. Selective epigenetic changes (e.g., changing methylation patterns) may also be possible in the future, but are currently impractical.

While a number of different adult pluripotent stems cell sources could be used herein, one important aspect of the invention lies in generating cells for treating sick sinus syndrome and other arrhythmias in humans. The preferred source of stem cells are autologous cells, such as e.g., adipose tissue derived regenerative cells from the same patient that needs repair of arrhythmias. Adipose tissue is preferred as containing a high number of these early pluripotent cells that are able to undergo with the appropriate sequential induction to form non-contractile, but electrically special cells such as pacemaker and Purkinje cells, that associate to form a sinuatrial body. Adipose tissue is readily available from the patient without the discomfort associated with tapping bone marrow sources or using allogenic cells obviating any rejection issues. In the future, when more and more patients have stored e.g., umbilical cord blood and/or umbilical or placenta derived stems cells and the like, other types of stem cells may be preferred in a matched allogenic transplant procedure, but at the current time, for few patients currently these resources exist yet.

No one has to this point been able to use uncultured or cultured adult, i.e. non embryonic and non-iPS stem cells, for the creation of induced sinoatrial cells that show the characteristics of pacemaker cells both on the morphological level and the functional level. The use of these cells represents a tremendous advantage over embryonic stem cells because they can be autologous, eliminating rejection problems, and are readily available, unlike embryonic stem cells. Furthermore, induced pluripotent stem (iPS) cells may not be safe—several reports recently indicated that such cells are close to cancer cells.

Allogenic cells may also be suitable, although immunomodulatory drugs are typically required if the HLA pattern does not match. However, such cells are in use today, and may be more amenable to use in the future as more and more banks collect and store cord blood, cord tissue stem cells, etc. and the stem cells generated thereby, particularly where libraries of hundreds and thousands of different HLA patterns can be collected and cryopreserved, so that the probability of a matched allogeneic transplant increases. Alternatively, a library of induced pacemaker/Purkinje cells can be generated in advance, so at the time of need, these cells will be readily available for transplantation.

Furthermore, we have described the invention using human wild type genes, but other sources may be used as appropriate for the species. Codon optimization can also be performed to optimize expression.

The invention includes and one or more of the following embodiments, in any combination(s) thereof:

A method of inducing stem cells, especially adult stem cells to differentiate into an induced non-contractile cardiomyocyte cell types, such as pacemaker, Purkinje and sinoatrial body cells, said method comprising inducing the sequential expression of SHOX2 > TBX5 > HCN2 in a population of stem cells in order to reprogram said stem cells, and growing said reprogrammed cells until cardiac pacemaker cells and Purkinje cells form and associate into an induced sinoatrial body.

A method of repair of the natural pacemaker in the heart, said method comprising obtaining stems cells from a patient with a malfunctioning pacemaker, inducing sequential expression of SHOX2 > TBX5 > HCN2 in said stem cells to form reprogrammed cells, and growing said reprogrammed cells until cardiac pacemaker cells and Purkinje cells form and associate into an induced sinoatrial body, and introducing said induced sinoatrial body into a heart of said patient.

A method as herein described, wherein said stem cells are autologous stem cells from the patient's own body.

A method as herein described, wherein said stem cells are autologous adipose derived stem cells. Cord blood, cord tissue and bone derived stem cells could also be used.

A method as herein described, comprising inducing the sequential expression of SHOX2 > TBX5 > TBX3 > TBX18 > HCN2, or the sequential expression of SHOX2 > TBX5 > [TBX3 and/or TBX18 in either order] > HCN2, or the sequential expression of SHOX2 > [TBX5 or TBX3 or TBX18] > HCN2.

A method as herein described, wherein said inducing step uses one or more expression vectors, preferably a lentiviral vector, encoding the needed proteins.

A method as herein described, wherein said inducing step uses the sequential application of mRNA as the recited proteins.

An induced sinoatrial body made by any method herein.

A composition comprising a population of reprogrammed cells formed from stem cells transformed with expression constructs allowing the sequential expression of SHOX2 > TBX5 > HCN2, thus forming said reprogrammed cells. Preferably, the population is containing in a pharmaceutically acceptable liquid excipients and/or a cell support medium that functions to safely support said cells until use, or even a cell growth medium, that allows their growth (growth meaning cell division) until use.

A composition comprising a population of reprogrammed cells formed from stem cells transformed with expression constructs allowing the sequential expression of SHOX2 > (TBX5 and TBX3 and TBX18) > HCN, thus forming said reprogrammed cells A composition comprising a population of reprogrammed cells formed from stem cells transformed with expression constructs allowing the sequential expression of SHOX2 > TBX5 > TBX3 > TBX18 > HCN2, thus forming said reprogrammed cells An expression vector comprising inducible genes encoding proteins SHOX2, TBX5 and HCN2, such that each gene can be sequentially induced.

An expression vector comprising a first inducible promoter operably linked to a gene encoding SHOX2, a second inducible promoter operably linked to a gene encoding TBX5, and a third inducible promoter operably linked to a gene encoding HCN2, such that each gene can be sequentially induced by first, second and third inducers. Likewise, the other genes described herein can be similarly employed.

A method as herein described, further including separating said pacemaker cells and said Purkinje cells by size sorting. The separated cells can also be used for treatments, for example, Purkinje cells can be used to treat tachycardiac arrhythmia and pacemaker cells can be used to treat sick sinus syndrome.

A method as herein described, wherein said adult stem cells are obtained from a patient with a tachycardiac arrhythmia, and wherein said separated Purkinje cells are administered to said patient in an amount sufficient to treat said tachycardiac arrhythmia.

A method as herein described, wherein said adult stem cells are obtained from a patient with sick sinus syndrome, and wherein said separated pacemaker cells are administered to said patient in an amount sufficient to treat said sick sinus syndrome.

Any treatment method herein wherein a defective sinoatrial body is ablated before said administration step. These can be ablated with heat, lasers, cryogenically, and the like. In such as method, the heart will only be guided by the induced sinoatrial body or the induced cells, and no conflicting electrical signals would be present.

As used herein, "an induced sinoatrial body" consists of reprogrammed stem cells that have been induced to form pacemaker and Purkinje cells that have then associated to form functional interconnections and produce an induced sinoatrial body that generates funny current and can induce heart beating. Functional interconnection and electrophysiological properties of pacemaker and Purkinje cells are associated with the expression of specific cell membrane junctions and ion channels; specifically in terms of cardiac conduction cells, including CX30.2 and HCN4 (FIG. 10, 11).

As used herein, a pacemaker cell is a large primarily round (>50 μm) cell with several spider-like protrusions that has the ability to spontaneously depolarize (FIG. 7, 8).

As used herein, a "Purkinje cell" is a small (<20 μm across the diameter of the main cell body), cell that forms specific chains with each other and spontaneously orient itself in chains and channels, will surround and form interconnections with a pacemaker cell (FIG. 7, 8, 9).

As used herein, "inducing" the expression of certain genes in stem cells does not imply any particular methodology, and is not limited to the use of inducible promoters. Instead, any means of turning on gene expression can be used, including the use of expression vectors, naked DNA or RNA or protein, induced epigenetic changes, and the like. It does not include those natural cells that already demonstrate expression of the recited gene/proteins, but only stems cells that have been re-programmed to do so by the hand of man.

As used herein, "stems cells" or "regenerative cells," includes multipotent and pluripotent stems cells, as well as other types of cells that can be successfully reprogrammed to differentiate into the cell types described herein. These are cells that are not yet differentiated, or have been dedifferentiated, and thus have the potential to either form all cell types, or a multiplicity of cell types.

"Adult stem cells" are typically multipotent stem cells derived from a non-infant person, and does not imply any particular age of the donor. Also known as somatic stem cells, they can be found in children, as well as adults.

As used herein, "autologous" means cells derived from the patient or a genetically identical patient. "Allogenic" refers to cells derived from the same species, but having a different genotype.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention. Elements of this type would include e.g., buffers, chelators, nutrients, instructions for use, and the like.

The following abbreviations are used herein:

| ABBREVIATION | TERM |
| --- | --- |
| αMEM | MEM with Earles balanced Salts |
| ADST | Adipose derived stem cells |
| cDNA | Copy DNA |
| DNA | Deoxyribonucleic acid |
| EKG | Electrocardiogram, also ECG |
| FBS | Fetal bovine serum |
| MEM | Minimum-essential medium |
| PBS | Phosphate buffered saline |
| PCR | Polymerase chain reaction |
| qPCR | Quantitative PCR |
| RNA | Ribonucleic acid |
| SAN | sinoatrial node |

BRIEF DESCRIPTION OF THE DRAWINGS

FIG. 1B. ELECTROPHYSIOLOGY OF THE HEART: Electrical system of the heart and EKG trace in detail.

FIG. 2. GENE ACTIVATION SEQUENCE: Schematic algorithm representing the critical genes involving in different stages of cardiac pacemaker cell lineage development.

FIG. 11. DAPI and CX30.2 IN LARGE CELLS. Expression of CX30.2 in both small and large spider shaped cells.

FIG. 13. RNA EXPRESSION LEVELS. mRNA expression levels of specific marker genes of cardiac Purkinje cells in ADSCs transfected with different combinations of pacemaker inducing factors, 2 weeks after the initiation of induction.

FIG. 14. RNA EXPRESSION LEVELS CONT. mRNA expression levels of specific marker genes of cardiac pacemaker cells in ADSCs transfected with different combinations of pacemaker inducing factors, 2 weeks after the initiation of SHOX2, TBX5 and HCN2 induction.

DETAILED DESCRIPTION

The invention provides novel methods of making pacemaker cells and Purkinje cells or sinoatrial nodes (SANs);

the pacemaker cells, Purkinje cells, and SANs made thereby; and methods of using same, e.g., to replace or supplement damaged pacemakers and Purkinje fibers in the heart of patients, such as human patients. The cells can be surgically delivered directly or by catheter based injection to the place where they are required. For the repair of the sinus node for example, a catheter based injection of a few thousand cells into the damaged and reduced functioning sinus node is sufficient to effect repair.

For the repair of tachycardic arrhythmias, Purkinje cell are injected into the slow conducting zone, such as the border zone of an infarction, in order to accelerate the speed of conduction in this arrhythmogenic substrate and thereby to close the re-entry pathway by accelerating the circulating impulse in such a way that it meets refractory myocardium and the re-entry is interrupted.

Preferably, the cells are made from autologous cells, using any available stem cell source from the patient, such as bone marrow derived stem cells or adipose derived or blood, skin and umbilical cord tissue derived stem cells.

Lentiviral-Based Reprogramming

To induce ADSCs to differentiate into cardiac pacemaker cells, they are sequentially transfected with different combinations of cardiac pacemaker inducing factors including SHOX2, TBX5, TBX3, TBX18 and HCN2 by applying a lentiviral vector system. The lentiviral vector is under the control of a switch, for example a doxycycline switch.

Figure 1A:
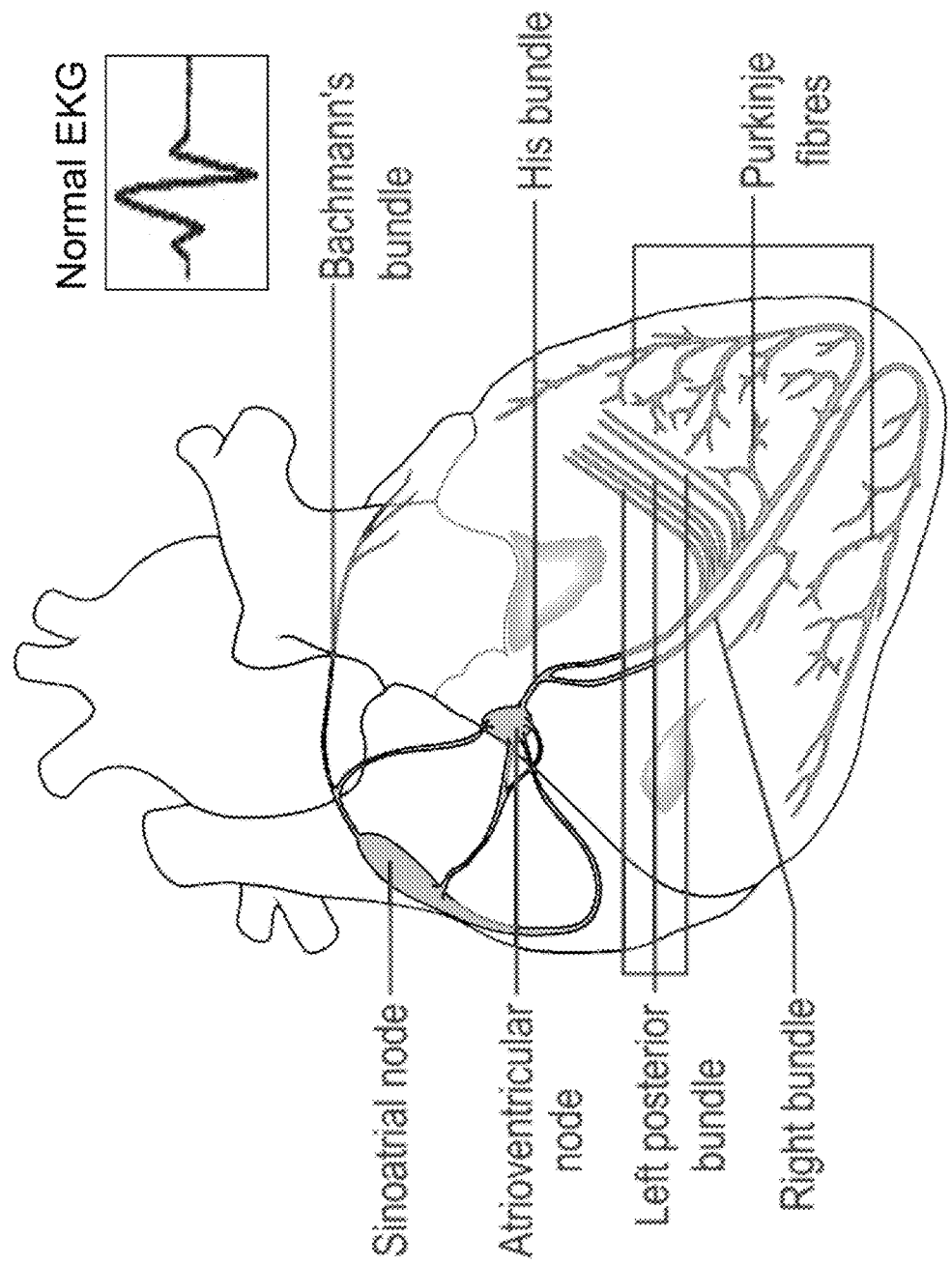
FIG. 1A. ANATOMY OF THE HEART: Diagram of the anatomy of a heart in cross section, with EKG trace (upper right).
Figure 3:
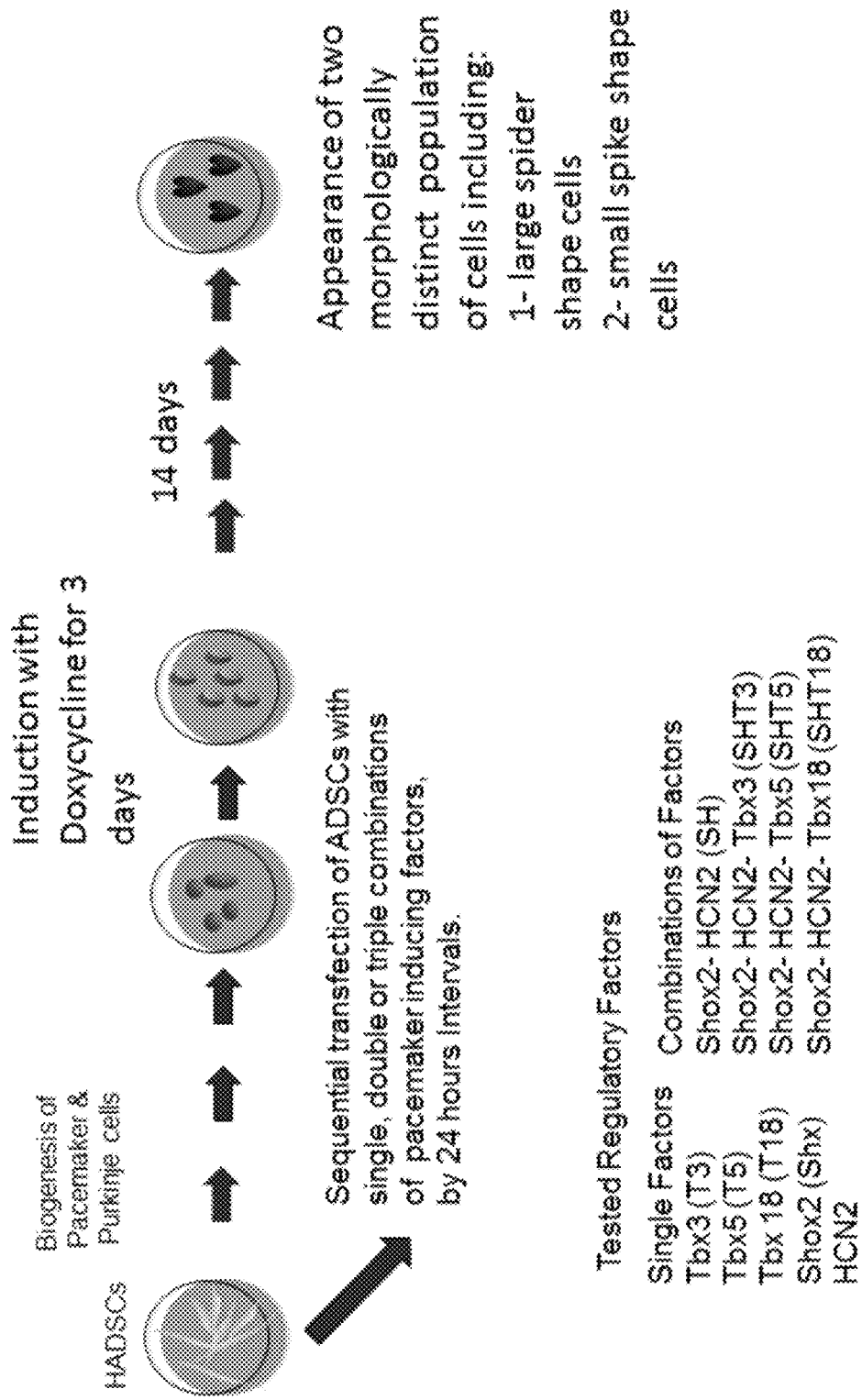
FIG. 3. EXPERIMENTAL OVERVIEW: Schematic diagram, representative of sequence of experimental procedures for generation of cardiac pacemaker cells.

The expression of cardiac pacemaker inducing factors was achieved by lentiviral vectors, applied to the cells in the sequential way in 24-hour intervals (FIG. 3). Cells were cultured in α-MEM supplanted with 5% horse serum, 2 mM glutamine, 0.1 mM non-essential amino acids. Cultures were treated daily with 400 ng/ml doxycycline for 3 days, then sustained for 2 weeks in α-MEM with above mentioned supplements. Daily microscopic observation of cells was performed to study the morphological changes of cells after the transfection. RNA samples were collected from different experimental groups at day 14 after the initiation of Doxycycline induction.

TABLE 1

List of experimental groups by controlled expression of single, double and triple combinations of pacemaker inducing factors in ADSCs

| Experimental Groups' Name | Description of Treatments |
| --- | --- |
| T3 | ADSCs transfected with TBX3 only |
| T5 | ADSCs transfected with TBX5 only |
| T18 | ADSCs transfected with TBX18 only |
| HCN-2 | ADSCs transfected with HCN2 only |
| SHOX2 | ADSCs transfected with SHOX2 only |
| SH | ADSCs transfected with double combination of SHOX2 and HCN2 |
| SHT-3 | ADSCs transfected with triple combination of SHOX2, TBX3 and HCN2 |
| SHT-5 | ADSCs transfected with triple combination of SHOX2, TBX5 and HCN2 |
| SHT-18 | ADSCs transfected with triple combination of SHOX2, TBX18 and HCN2 |

Human ADSCs (hADSCs) were obtained from INGENERON® (Houston, Tex.). Adipose tissue from donors aged 30-40 years old were obtained with informed consent under a tissue acquisition protocol approved by the Institutional Review Board. The ADSCs were prepared from lipoaspirate acquired from donors undergoing elective lipoplasty. The hASDCs were isolated as described previously.

Briefly, fat tissue was minced and incubated for 30 min at 39° C. with Matrase (INGENERON®) at a concentration of 1 unit per gram of fat tissue in Ringer solution in the Transpose RT™ processing unit (INGENERON®). The processed tissue was subsequently filtered through a 100 µm filter and centrifuged at 450 g for 10 min. The supernatant containing adipocytes and debris were discarded, and the pelleted cells were washed twice with Hanks' balanced salt solution (CELLGRO™) and finally suspended in growth media. The process is described in detail by instructions for use of InGeneron Transpose RT™ system (INGENERON®). Growth media contained alpha-modification of Eagle's medium (CELLGRO™), 20% FBS (ATLANTA BIOLOGICALS™), 2 mM glutamine, 100 units/ml penicillin with 100 µg/ml streptomycin (CELLGRO™).

Adherent cells were called hADSCs and grown in culture flasks at 37° C. in a humidified atmosphere containing 5% $CO_2$ followed by daily washes to remove red blood cells and non-attached cells. On reaching 80% confluence, cells were detached applying Trypsin solution 0.25% and seeded at the density of 3000 cells/cm² in fresh cell culture flasks.

Figure 4:
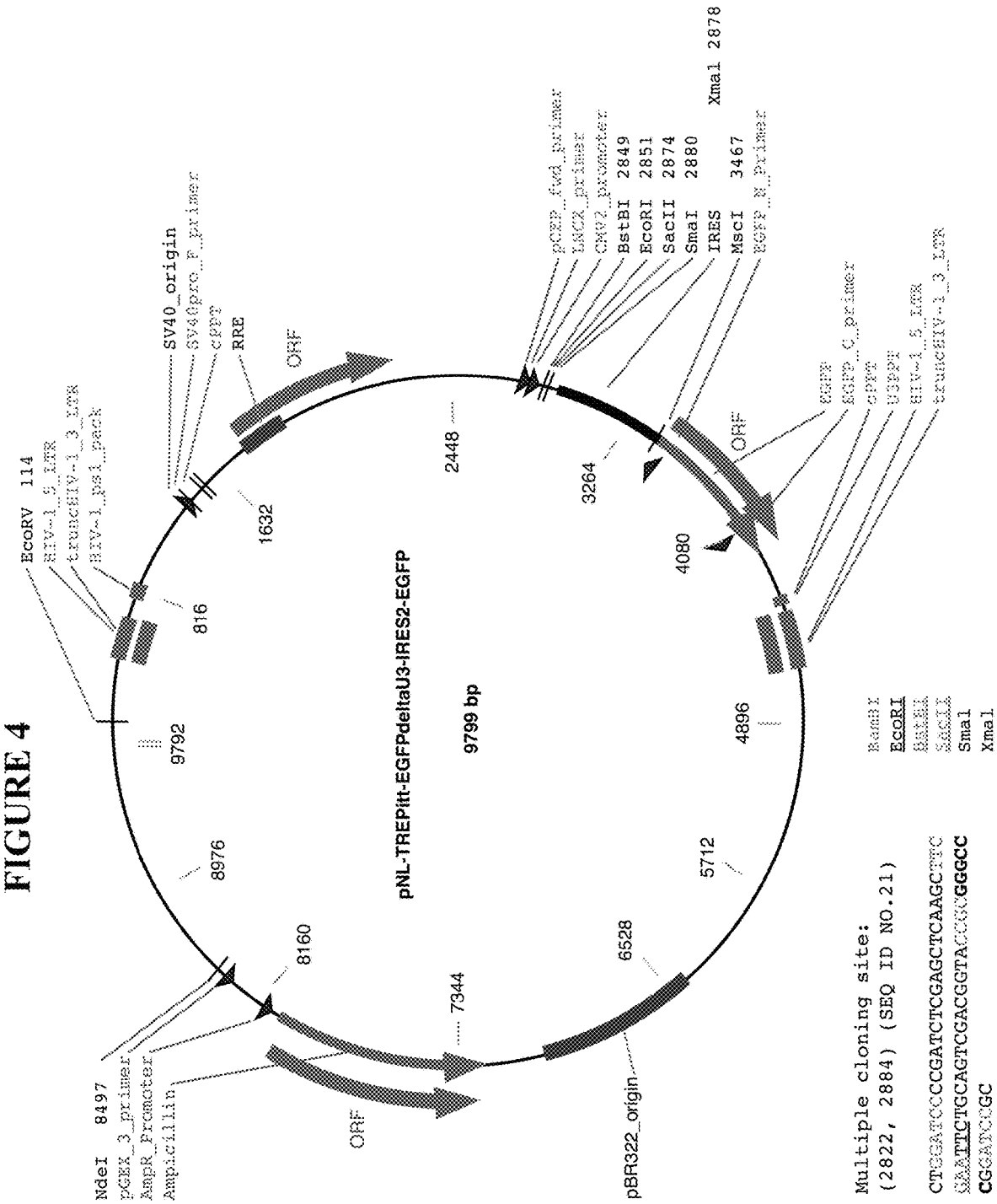
FIG. 4. VECTOR MAP: PNL-TREPiTT-EGFP deltaU3-IRES2-EGFP plasmid used as an expression vector for TBX3, TBX5, TBX18, HCN2, SHOX2 constructs.

To differentiate ADSCs into cardiac pacemaker cells, the ADSCs were transfected with different combinations of cardiac pacemaker inducing factors including SHOX2, TBX3, TBX5, TBX18 and HCN2 using a lentiviral vector system (Table 1). The lentiviral vector used herein includes packing vector psPAX2 and envelope vector pMDS2.G (ADDGENE™) (Islas, 2012). In addition, a Doxycycline controlled transactivator (rtTA2) was used as a transcriptional inductive switch of the system. Plasmid PNL-TREPiTT-EGFP delta U3-IRES2-EGFP (FIG. 4) was used as a backbone vector for every single gene. A commercial cell line—293FT—was used for viral packaging. The 293FT cell line is a fast-growing, highly transfectable clonal isolate derived from human embryonal kidney cells transformed with the SV40 large T antigen and is available from THERMO FISCHER SCIENTIFIC®.

Briefly viral particles were produced in 293 T cells transfected with psPAX2, pMDs2.G vectors and plasmids containing every single gene of interest including SHOX2, TBX3 TBX5, TBX18, HCN2. Reprogramming of about 80% confluent ADSCs into proliferative state were accomplished by infection with different combinations of the viral particles containing SHOX2, TBX3, TBX5, TBX18, HCN2 vectors according to the predefined experimental groups (see Table 1). The 4 and 5 gene combinations also present good preliminary results.

Transfected cells were cultivated in large tissue culture plates by α-MEM (INVITROGEN®) supplemented with 5% (vol/vol) horse serum, 0.1 mM non-essential amino acids, 2 mM L-glutamate.

The stable integration and mRNA expression of each gene construct were confirmed 72 hours after the transfection using PCR.

To study any changes occurring in the cells after the transfection, delicate microscopic observation of cells were performed every day. Representative data are shown herein, that belonging to the triplet combination of the sequential transfections of SHOX2>TBX5>HCN2.

Figure 5:
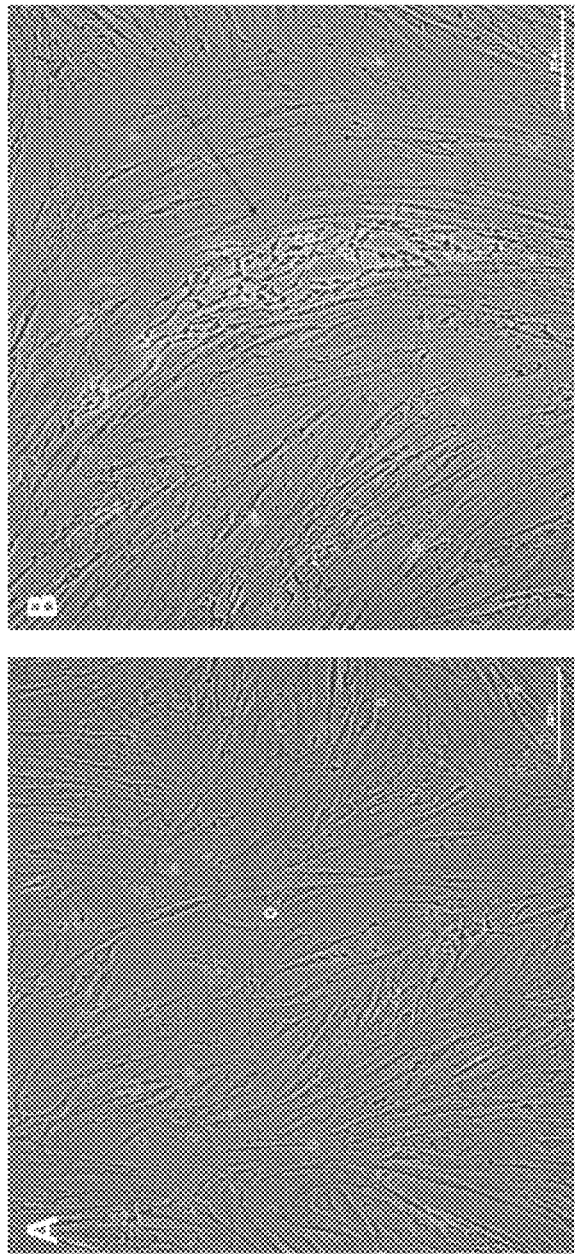
FIG. 5. ADSC BEFORE AND AFTER TRANSFECTION: Changes in the morphology of ADSCs after transfection with cardiac pacemaker inducing factors SHOX2, TBX5 and HCN2 from the typical fibroblastic like morphology of ADSCs (A) to the colonies of small network forming cells (B), see arrow, 7 days after initiation under a doxycycline dependent switch.
Figure 6:
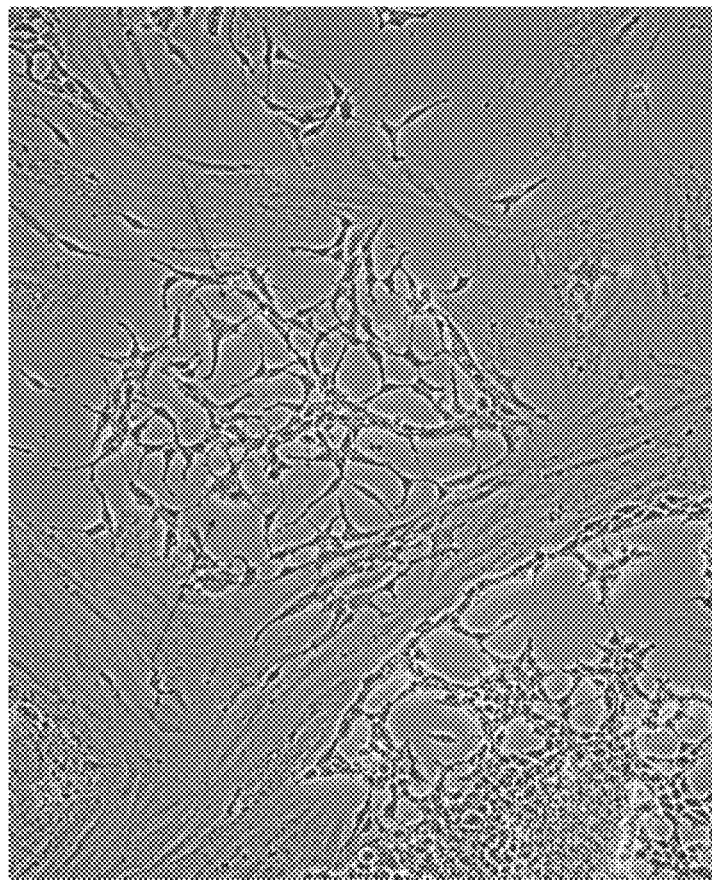
FIG. 6. CHANGING MORPHOLOGY: Changes in the morphology of ADSCs after transfection with cardiac pacemaker inducing factors SHOX2, TBX5 and HCN2 from the typical fibroblastic like morphology of ADSCs to the colonies of small and large network forming cells within 1 week after initiation of doxycycline switch controlled induction.

Starting from week 2 after Doxycycline triggered treatment genetically programmed pacemaker cells from different experimental groups initiated to convert their fibroblastic like morphology and formed new colonies containing a particular network forming cell type with several large spike shape projections. The sequential transfections of SHOX2>TBX5>HCN2 are shown in FIG. 5, 6.

Figure 7:
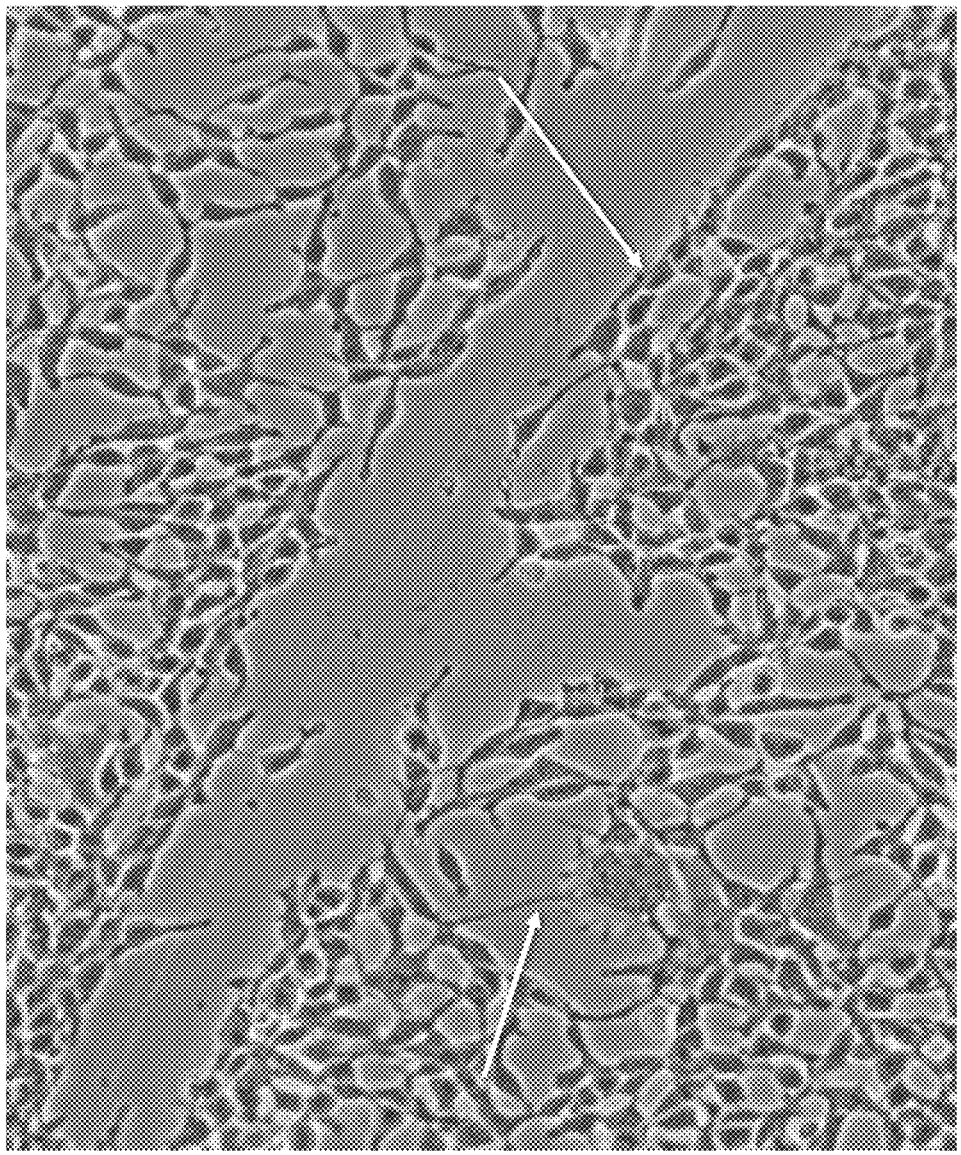
FIG. 7. CELL TYPES AND ALIGNMENT: Observation of 2 different cell types in culture plate of ADSCs transfected with SHOX2, TBX5 and HCN2. Right-arrow—Small cell population with spike shape projections. Small cells start to form a special aligned growth pattern and make channel like structures. Left arrow—Larger cells with special spider shape morphology.
Figure 8:
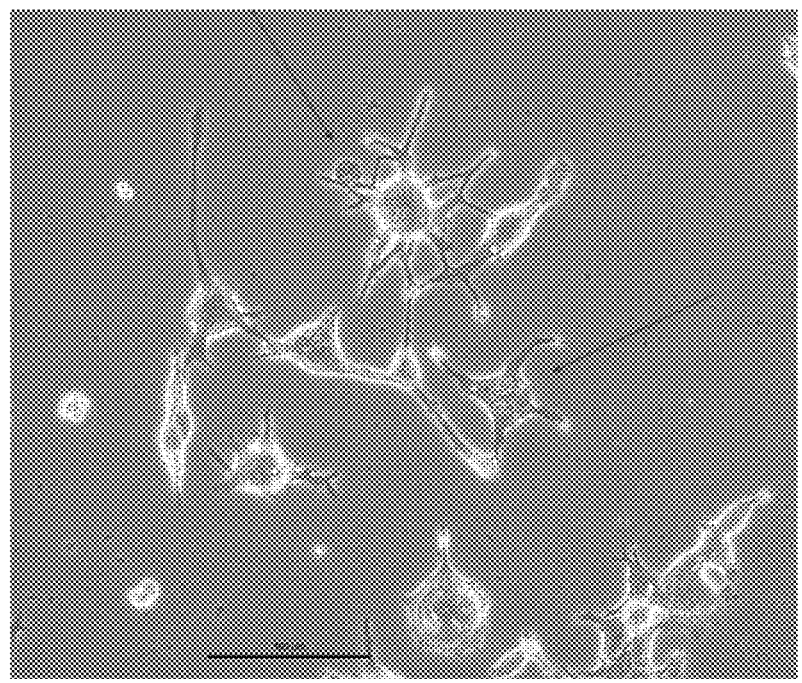
FIG. 8. CLOSEUP OF LARGE CELLS: Appearance of typical spiderlike morphology of large cells (>50 μm) within 14 days after initiation of doxycycline controlled induction of SHOX2, TBX5 and HCN2.
Figure 9:
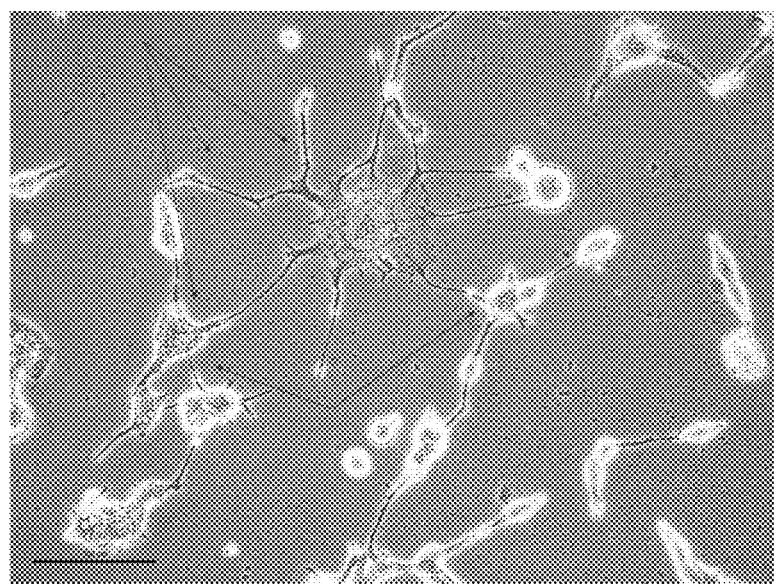
FIG. 9. NETWORKS: Large spider shape cells start to form networks with each other and with small cells within 3 weeks after induction of SHOX2, TBX5 and HCN2.

During the differentiation period in various experimental groups, gradually two different types of cells appeared, including a particular large spider shape cell type and small spindle shape cells with long spike like projections. FIG. 7, 8 shows the appearance of the two cell types in the triple sequential transfections of SHOX2>TBX5>HCN2. Subsequently, both populations of spindle and spider shape cells began to form highly interconnected networks with each other (FIG. 9). In addition small spike shape cells started to form particular, highly aligned growth patterns (see linear groove forming in FIG. 7, likely corresponding to Purkinje cell networks in the natural conduction system of heart.

According to the results of previous studies on isolation of pacemaker cells from fetal SAN, spider shape morphology has been defined as a typical morphology of pacemaker cells. Therefore, our ordered transfection experiments showed that the triplet sequential transfections of SHOX2>TBX5>HCN2 made cells with a morphology very much like natural pacemaker cells.

Although not shown herein, the similar observations were made in different groups of ADSCs transfected with various combinations of pacemaker inducing factors. However, more robust morphological changes toward the typical morphology of cardiac conduction cells were observed in ADSC groups transfected with TBX transcription factors (particularly TBX5) in comparison with the groups transfected with individual or double combinations of SHOX2 and HCN2. The most robust morphological changes were observed in ADSCs group transfected with triple combinations of SHOX2, TBX5 and HCN2, and therefore these results are shown in part herein. Similar results were observed in expression of molecular markers of cardiac conductive system by qPCR assay (FIG. 13, 14).

Results of earlier in vivo studies on identifying the main molecular regulators of cardiac conduction system development identified T-box proteins as essential factors for cardiac conduction system morphogenesis as well as the up-regulation of genes encoding the ion channel proteins that contribute to the electrophysiological functionality of cardiac conduction cells.

Hoogaars e al., 2007 indicated that TBX3 controls the sinoatrial node gene program and imposes pacemaker function on the atria. Results of other studies indicating TBX5 is a critical transcription factor regulating developmental networks required for maturation of and functionality of cardiac conduction cells.

Results of genome wide associate studies (GWAS) have identified numerous loci associated with the developmental processes of human cardiac conduction system including TBX5 and ion channels. Expression of ion channels is critical for electrophysiological functionality of the system. Arnold et al., 2012 found that deletion of TBX5 results in severe malfunction in cardiac conduction system including loss of fast conduction, arrhythmias and sudden death.

In addition based on the results of genome wide associate studies (GWAS) a molecular link was identified between TBX5 and SCN5A (UNIPROT Q14524), aka NAV1.5, a key mediator of fast conduction system. Results of this study identified a TBX5-responsive enhancer downstream of SCN5A, which is sufficient for the lineage specification of ventricular conduction system (Arnolds, 2012).

The smaller cells correspond to Purkinje cells, as determined by spindle like morphology and long cellular projections: Two weeks after transfection these small spindle like cells illustrated particularly a highly aligned growth pattern, including formation of multicellular strands and networks through the tight connection of individual cells to each other. These cells illustrated moderate levels of funny currents in single cell patch clump assay. According to the results of previous in vivo studies on isolation and characterization of various cardiac cell types, this particular strand and network forming growth pattern has been defined as the typical characteristics of Purkinje cells. Similar morphological properties were reported in a previous attempt for in vitro production of cardiac nodal cells through the overexpression of TBX3 in ESCs. In addition in agreement with our findings, results of previous studies on characterization of different types of cardiac conductive cells also revealed the lower levels of electrophysiological activity in cardiac Purkinje cells in comparison with the pacemaker cells.

The two cells types associate to form interconnected networks wherein one pacemaker cell is surrounded and connected to several Purkinje cells to form a network. The Purkinje cells have the purpose to act as amplifier and conductors of the initial spontaneous depolarization induced by the pacemaker cells. The formation of these interconnected networks is closely correlated with the expression of specific membrane junctions and ion channels of cardiac conduction cells including CX30.2 and HCN4, essential for the electrophysiological functionality of cells. HCN4, which is a member of hyperpolarization activated cyclic nucleotide-gated sodium channels, is required for If, the specific pacemaker current. CX30.2 is responsible for the cell-cell junctions and formation of networks between spontaneously depolarizing cardiomyocyte cells.

RNA-Based Reprogramming

Another successful way to induce a programmed pacemaker non-contractile cardiomyocyte cell is using a mRNA-based transfection method. This methodology has not yet been fully completed on all different inducing factors, but our current results suggest the method to be equally viable and effective.

Briefly, coding DNA sequence is amplified by PCR using specific primers. PCR products then are purified and the quality of the generated DNA is determined. Using the in vitro transcription (IVT) process, mRNA is generated from the DNA product. Subsequently, the product is purified and treated with phosphatase to remove 5'-triphosphates. After the additional purification and quality control of generated mRNA, transfection experiments will be performed.

To obtain, the DNA template for the IVT, all TBX18, TBX3 and HCN2 plasmids are amplified using PCR. Thereby, a poly T-tail of 120 thymidines (T) is added to the insert by using a reverse primer with a $T_{120}$ extension. Thus, after IVT, the generated mRNAs obtain a poly A-tail with a defined length. PCR reactions of 100 µl will are performed using e.g., HOTSTAR™ HIFIDELITY POLYMERASE KIT (QIAGEN®, Germany) and contained 0.7 µM of each forward and reverse primer, 1×Q-solution, 1×HOTSTAR™ HIFIDELITY PCR buffer, 50 ng plasmid DNA, 2.5 U HOTSTAR™ HIFIDELITY DNA polymerase.

Amplification is performed using e.g., the following cycling protocol: initial activation step at 95° C. for 5 min, followed by 25 cycles of denaturation at 95° C. for 45 s, annealing at 55° C. for 1 min, extension at 72° C. for 1 min and final extension at 72° C. for 10 min. PCR products will be purified using QIAQUICK™ PCR PURIFICATION KIT (QIAGEN®, Germany) according manufacturer's instructions and the DNA eluted using 20 μl nuclease-free water. The quality and purity of the DNA can be assessed by 1% agarose gel electrophoresis.

After the PCR, the genetic information is transcribed from DNA to mRNA in vitro using e.g., MEGASCRIPT® T7 Kit (LIFE TECHNOLOGIES®, Germany). The mRNA transcript then will be used to induce protein expression in cells. At first, 23 μl NTP/cap analog mixture containing 7.5 mM ATP, 1.875 mM GTP (both from MEGASCRIPT® T7 Kit), 7.5 mM Me-CTP, 7.5 mM Pseudo-UTP (both from TRI-LINK BIOTECHNOLOGIES™, CA), and 2.5 mM 3'-O-Me-m$^7$G(5')ppp(5')G RNA cap structure analog (NEW ENGLAND BIOLABS®, Germany) will be prepared and mixed thoroughly.

The IVT reaction mixture of 40 μl then will be assembled by adding 40 U RIBOLOCK™ RNase inhibitor (THERMO FISHER SCIENTIFIC), 1 μg PCR product, 1× reaction buffer and 1× T7 RNA polymerase enzyme mix. The IVT reaction mixture will be incubated at 37° C. for 3 hr in a thermomixer. To remove the template DNA, 1 μl TURBO™ DNase (from MEGASCRIPT® T7 Kit) is added to the IVT reaction mixture and incubated for 15 min at 37° C. Then, the reaction mixture is purified using RNEASY™ Mini Kit (QIAGEN) according to manufacturer's instructions. The modified mRNA will be eluted from the spin column membrane twice with 40 μl nuclease-free water.

The generated mRNA will be treated with Antarctic phosphatase (NEW ENGLAND BIOLABS®) to remove 5' triphosphates, which can be recognized by RIG-1, and lead to the immune activation. Furthermore, the phosphatase treatment prevents the recircularization in a self-ligation reaction. For this purpose, 9 μl of 10× Antarctic phosphatase reaction buffer is added to 79 μl of purified mRNA solution. Subsequently, 2 μl of Antarctic phosphatase (5 U/μl) is added to the reaction mixture and incubated at 37° C. for 30 min.

The treated mRNA can be purified using e.g., RNeasy Mini Kit (QIAGEN) according to manufacturer's instructions. The modified mRNA will be eluted from the spin column membrane twice with 50 μl nuclease-free water. The concentration will be measured using SCANDROP spectrophotometer (ANALYTIC JENA, Germany). The concentration of mRNA will be adjusted to 100 ng/μl by adding nuclease-free water. The quality and purity of synthesized modified mRNA will be determined by 1% agarose gel electrophoresis. The modified mRNA will be aliquoted and stored at −80° C. and used for transfections.

ADSCs will be cultivated in α-MEM media supplemented with 10% FBS (LIFE TECH.), 2 mM L-glutamine (PAA LABORATORIES, Austria), and 1% penicillin/streptomycin (PAA LAB.). Cells will be kept at 37° C. with 5% $CO_2$ and media will be changed every 3 days. Cells will be passaged using trypsin/EDTA (0.04%/0.03%, PROMO-CELL™, Germany). For performing of transfection experiments, $1.5 \times 10^5$ cells will be plated per well of 24-well plate. The cells will be incubated overnight at 37° C. in a cell incubator. Next day, transfection experiments can be performed.

Transfection of ADSCs with different mRNA of the invention are performed with LIPOFECTAMINE® 2000 (LIFE TECH.®). To determine the required amount of LIPOFECTAMINE® 2000 for forming of lipoplexes, different amounts of LIPOFECTAMINE® 2000, of 1, 2, 4, 6 μl, were used to transfect the cells. For transfection of one well of 24-well plate, 250 μl Opti-MEM I reduced serum media was prepared containing 2.5 μg of each mRNA of interest and respective amount of LIPOFECTAMINE® 2000 according to the manufacturer's instruction.

The components are gently mixed by pipetting. The transfection mixture then is incubated at room temperature for 20 min to generate lipoplexes for transfection. Cells will be washed with 250 μl DPBS/well, the transfection mixture pipetted into the well. After 4 hr incubation at 37° C. and 5% $CO_2$, the transfection mixture is replaced by 1 ml complete cell culture medium. Cells will be cultivated for 24 hr in the cell incubator and analyzed using flow cytometry.

To determine the required amount of mRNA for induction of protein expression, firstly different amounts of every eGFP-mRNA, 0, 0.5, 1, 1.5, 2, 2.5 μg, are used to perform the transfection of cells. For transfection of one well of 24-well plate, 250 μl Opti-MEM I reduced serum media with respective amount of mRNA and 1 μl of LIPOFECTAMINE® 2000 will be prepared.

The components are gently mixed and incubated for 20 min at room temperature. Cells will be washed with 500 μl DPBS/well and the transfection mixture will be added. Cells will be incubated for 4 hr at 37° C. and 5% $CO_2$. Afterwards, the transfection mixture will be aspirated and 1 ml complete cell culture medium will be added to the cells. Cells will be incubated for 24 hr in the incubator.

Using flow cytometry, the eGFP expression in the cells is verified. After determining the required amount of mRNA for induction of protein expression by eGFP, the same concentration is applied for the respective mRNA according to the invention.

Immunohistochemistry

For further characterization of induced pacemaker cells, immunohistochemistry (IHC) staining for the major maker genes of cardiac pacemaker cell lineages including CX30.2 and HCN4 were performed 2 weeks after the initiation of Doxycycline triggered induction.

Figure 10:
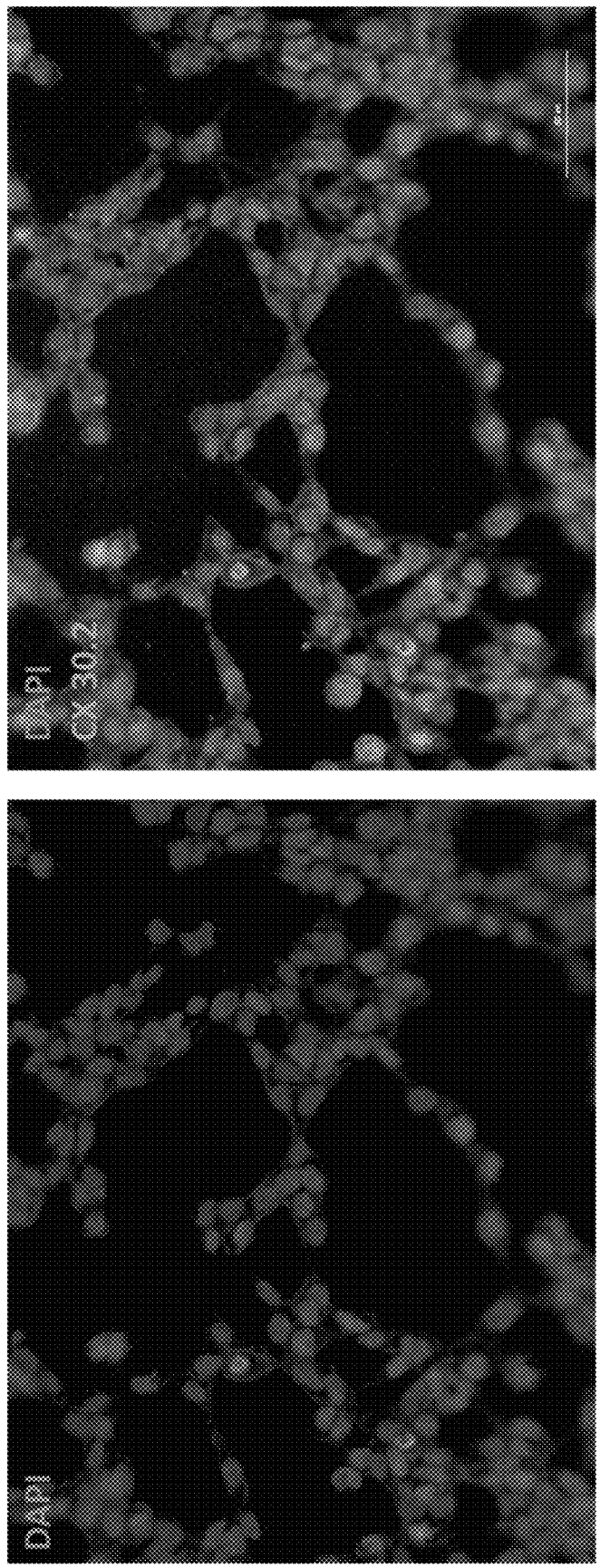
FIG. 10. DAPI AND CX30.2 IN SMALL CELLS. Expression of CX30.2 (a specific marker of pacemaker cell lineage) in small network forming cells. The blue DAPI stain lights up DNA, indicating the nucleus.

IHC staining was performed for two major marker genes respective of non-contractile cardiomyocytes including CX30.2 and HCN4. Results of IHC staining in cells sequentially transformed with the SHOX2>TBX5>HCN2 triplet revealed the expression of CX30.2 and HCN4 in both spindle and spider cell populations (FIG. 10, 11, 12). HCN4 is a member of hyperpolarization activated cyclic nucleotide-gated sodium channels required for If, the specific pacemaker current. CX30.2 is responsible for the cell-cell junctions and formation of networks between respective non-contractile cardiomyocytes.

Similar immunophenotype were also, observed in different groups of ADSCs transfected with other combinations of pacemaker inducing factors. However more robust changes in morphological properties and immunophenotype of transfected ADSCs towards the spontaneously depolarizing, non-contractile cardiomyocytes were observed in ADSC groups transfected with TBX transcription factors (particularly TBX5) in comparison to the groups transfected with individual or double combinations of SHOX2 and HCN2. The most robust changes in morphological properties and immunophenotype of transfected ADSCs toward the sinoatrial node's cells were observed by triple combinations of SHOX2, TBX5 and HCN2. It's also possible that TBX3 and TBX18 can be used in addition to or in replacement of TBX5, and that HCN4 can be used in addition to or in replacement of HCN2.

Expression Levels of Key Genes

To evaluate the effect of various combinations of cardiac pacemaker inducing factors on differentiation of ADSCs towards the different types of cardiac conduction cell lineages including pacemaker and Purkinje cells, mRNA expression level of specific marker genes of both cell lineages were analyzed.

To this end mRNA expression for a panel of downstream late stage markers of cardiac pace maker cells, including HCN1, HCN3, HCN4, SCN3B (UniProt Q9NY72), CX30.2 (properly known as GJC3, UniProt Q8NFK1) as well as Purkinje cells' specific marker genes including IRX3 (UniProt P78415), IRX5 (UniProt P78411), SEMA3B (UniProt Q6PI51), SCN10A (UniProt Q9Y5Y9), SHH (UniProt Q15465) were determined applying qPCR analysis on a mixed cell type population (e.g., cells were not first separated into pacemaker and Purkinje cells, although this experiment is planned).

Briefly total RNA was isolated using the QIAGEN's® RNEASY™ Kit and were reverse transcribed into cDNA using Superscript III (INVITROGEN®). Quantitative PCR were performed with the ABI Prism 7000 System Detection Sequence (SDS) and software (APPLIED BIOSYSTEMS®) using SYBR Green (APPLIED BIOSYSTEMS®) as the detector.

Figure 12:
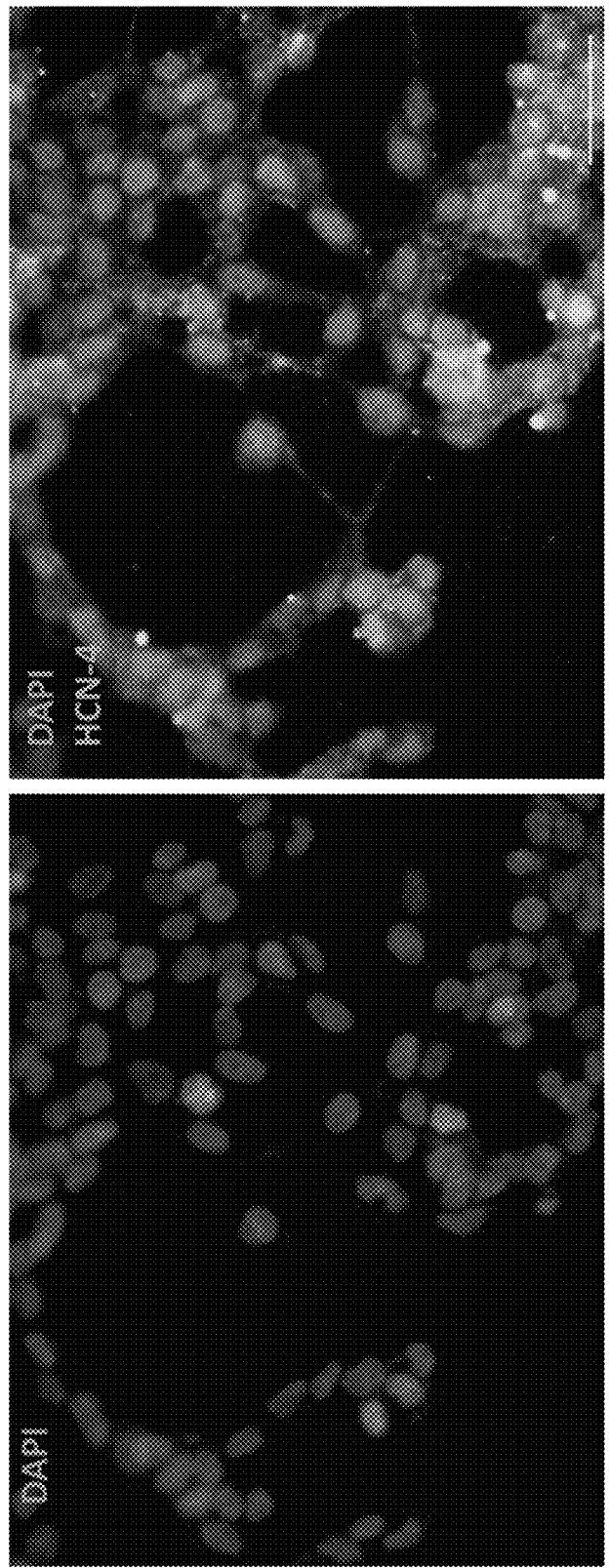
FIG. 12. DAPI AND HCN4 (a specific marker of pacemaker cell lineage) in both small and large cells.

The mRNA expression level for a panel of specific marker genes of cardiac pacemaker marker (Table 3 and FIG. 12) and Purkinje cells (Table 2 and FIG. 13) were analyzed thereby. Based on the results of qPCR analysis expression of marker genes of cardiac Purkinje cell can be observed in all different experimental groups transfected with different combinations of pacemaker inducing factors. However different combinations of cardiac inducing factors play various roles on up-regulation of downstream cardiac pacemaker marker genes including HCN1, HCN3, HCN4, SCN3B (UniProt Q9NY72), CX30.2 (GJC3, UniProt Q8NFK1).

For example the highest mRNA expression level of HCN3B, HCN3 and CX30.2 were observed in ADSCs transfected with triple combination of SHOX2, TBX5 and HCN2, while mRNA expression of HCN1 is more correlated with the up-regulation of TBX18. According to the results of this study, mRNA expression of HCN4 is highly correlated with the up-regulation of SHOX2. In addition moderate expression level of HCN4 was observed in ADSCs transfected with triple combinations of SHOX2, TBX5 and HCN2. All together based on the results of qPCR, transfection of ADSCs with triple combinations of SHOX2, TBX5 and HCN2 leads the most consistent up-regulation of different marker genes of cardiac conductive cells. It can be concluded that the most robust changes in gene expression pattern of transfected ADSCs towards the spontaneously depolarizing, non-contractile cardiomyocytes were observed in ADSC groups transfected with TBX transcription factors (particularly TBX5) in comparison to the groups transfected with individual or double combinations of SHOX2 and HCN2. The most robust and consistent changes in gene expression pattern of transfected ADSCs toward the spontaneously depolarizing, non-contractile cardiomyocytes were observed by triple combinations of SHOX2, TBX5 and HCN2.

Generally it can be concluded that triple combinations of SHOX2, TBX5 and HCN2 can be applied effectively for generation of both cell types of cardiac conductive system including Purkinje and Pacemaker cells.

TABLE 2

List of forward (F) and reverse (R) primer sequences for specific marker genes of cardiac Purkinje cells

| Gene name | Primer's name | Nucleotide sequence of primer |
|---|---|---|
| Iroquois homeobox-5 (IRX3) | IRX3 F (SEQ ID NO. 1) | GAGGGAAACGCTTATGGG AGC |
| | IRX3 R (SEQ ID NO. 2) | CGCCGTCTAAGTTCTCCA AATC |
| Iroquois homeobox-5 (IRX5) | IRX5 F (SEQ ID NO. 3) | TCAGCGACTCGGATTTTA AGGA |
| | IRX5 R (SEQ ID NO. 4) | GGAGGCGGCGAATGGATA A |
| Semaphorine (SEMA3B) | SEMA3B F (SEQ ID NO. 5) | ACATTGGTACTGAGTGCA TGAAC |
| | SEMA3B R (SEQ ID NO. 6) | GCCATCCTCTATCCTTCC TGG |
| Sodium channel voltage gated 10 (SCN10A) | SCN10A F (SEQ ID NO. 7) | TCCCTCGAAACTAACAAC TTCCG |
| | SCN10AR (SEQ ID NO. 8) | TCTGCTCCCTATGCTTCT CTC |
| Sonic Hedge hog (SHH) | SHH F (SEQ ID NO. 9) | CCAAGGCACATATCCACT GCT |
| | SHH R (SEQ ID NO. 10) | GTCTCGATCACGTAGAAG ACCT |

TABLE 3

List of forward (F) and reverse (R) primer sequences for specific marker genes of cardiac Pacemaker cells

| Gene name | Primer's name | Nucleotide sequence of primer |
|---|---|---|
| Hyperpolarization activated cyclic nucleotide ion channel-1 (HCN1) | HCN1 F (SEQ ID NO. 11) | CATGCCACCGCTTTAATC CAG |
| | HCN1 R (SEQ ID NO. 12) | ATTGTAGCCACCAGTTTC CGA |
| Hyperpolarization activated cyclic nucleotide ion channel-3 (HCN3) | HCN3 F (SEQ ID NO. 13) | AGCAGTGGAAATCGAGCA GG |
| | HCN3 R (SEQ ID NO. 14) | GGTCCCAGTAAAACCGGA AGT |
| Hyperpolarization activated cyclic nucleotide ion channel-3 (HCN3) | HCN4 F (SEQ ID NO. 15) | GAACAGGAGAGGGTCAAG TCG |
| | HCN4 R (SEQ ID NO. 16) | CATTGAAGACAATCCAGG GTGT |
| Sodium Channel, Voltage gated 3b (SCN3B) | SCN3B F (SEQ ID NO. 17) | GCCTTCAATAGATTGTTT CCCCT |
| | SCN3B R (SEQ ID NO. 18) | CTCGGGCCTGTAGAACCA T |
| Connexin 30.2 (CX30.2) | CX30.2 F (SEQ ID NO. 19) | TGGAGTCAGCGGTTTCTG TC |
| | CX-30.2 R (SEQ ID NO. 20) | TTGTGTCTTCTGGTGCTC TCT |

Patch Clamp Assays

To further verify the functionality of genetically programmed pacemaker cells their electrophysiological properties we performed single-cell patch clamp experiments to measure the currents generated by the cells (White, 2005).

Whole cell voltage-clamp experiments were carried out using the standard patch-clamp method. Recording electrodes were made from 1.5-mm thin-walled borosilicate glass (no. 7052, GARNER GLASS™, CA) using a Flaming-Brown microelectrode puller (P-97, SUTTER INSTRUMENTS™, CA) and heat polished before use. Each of the pipettes have a tip resistance of 2-5 MΩ when filled with internal solution. Recordings were performed using an Axoclamp 2B patch-clamp amplifier (AXON INSTRUMENTS™; CA). Data were filtered at 2 kHz, and data acquired using Clampex 8 software (AXON INSTRUMENTS™).

Patch pipettes were pulled from borosilicate glass and heat polished. They had a resistance of 2-5 MΩ when filled with intercellular solution.

For current-clamp recordings, the intercellular solution was containing 10 mM NaCl, 130 mM potassium aspartate, 0.04 mM $CaCl_2$. 3 mM Mg-ATP, 10 mM HEPES. pH was adjusted to 7.2 with KOH. The extracellular (bath) solution contained 140 mM NaCl, 5.4 mM KCl, 1.8 mM $CaCl_2$, 1 mM $MgCl_2$, 10 mM glucose, and 5 mM HEPES at pH 7.4.

Figure 15:
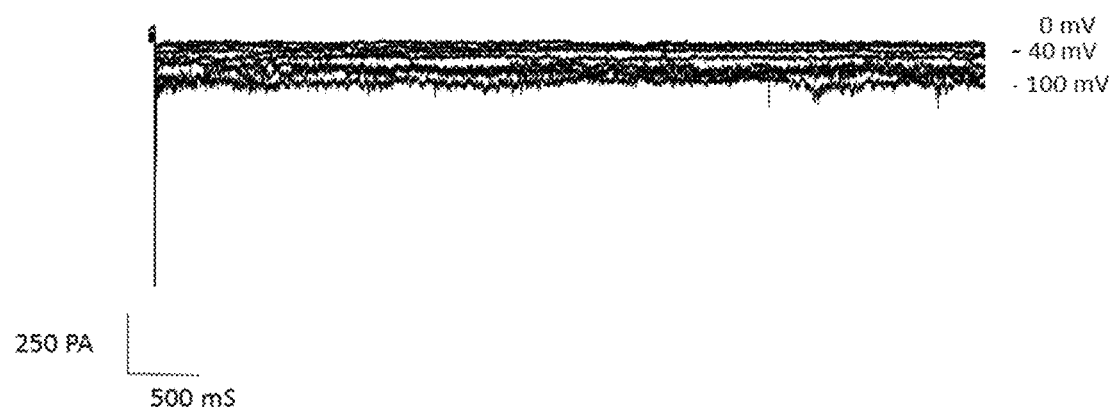
FIG. 15. SINGLE CELL VOLTAGE CLAMP EXPERIMENTS, FUNNY CURRENT CONTROL CELLS: Representative funny current (If) recorded from ADSCs (Control 2) cells. The If currents were elicited with voltage steps from −100 mV to −40 mV for 500 mS with 10 mV increment from a holding potential of −40 mV.
Figure 16:
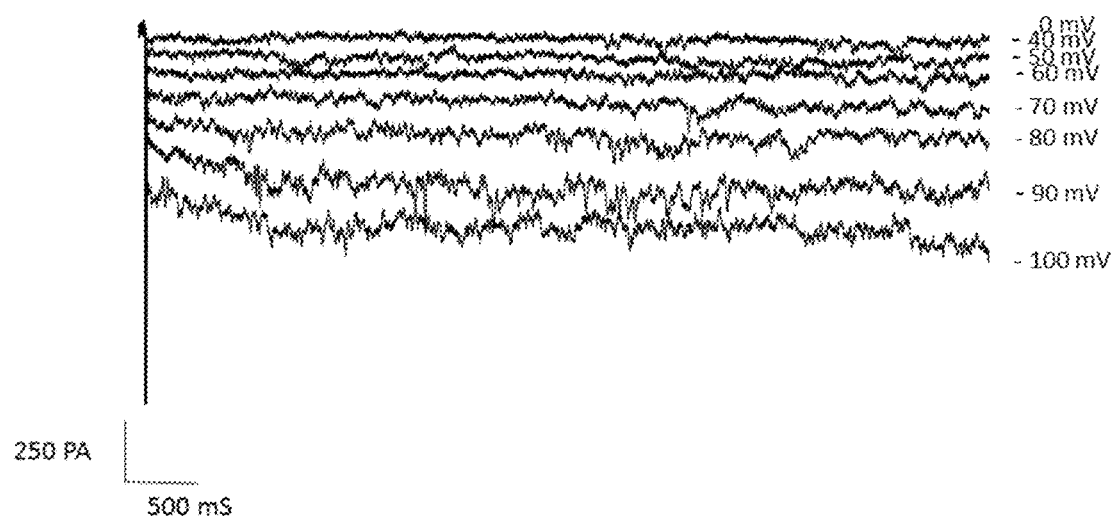
FIG. 16. FUNNY CURRENT IN SMALL CELLS: representative funny current (If) recorded from small size fraction (<20 μm cell size) of ADSCs transfected with SHOX2, TBX5, and HCN2. The If currents were elicited with voltage steps from −100 mV to −40 mV for 500 mS with 10 mV increment from a holding potential of −40 mV.
Figure 17:
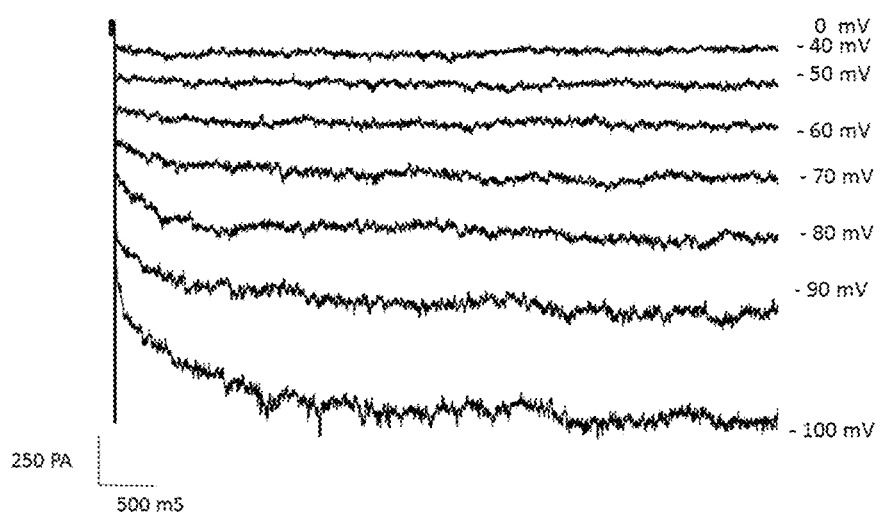
FIG. 17. FUNNY CURRENT IN LARGE CELLS. Representative funny current (If) recorded from large size fraction (>50 μm cell size) of SHOX2, TBX5, HCN2 transfected ADSCs. The If currents were elicited with voltage steps from −100 mV to −40 mV for 500 mS with 10 mV increment from a holding potential of −40 mV.

Funny Current (If) density was measured with voltage steps from −100 mV to −40 mV for 500 mS with 10 mV increments from a holding potential of 40 mV. Because an important characteristic of cardiac a pacemaker cell is the expression of an inward funny current (If). According to the results of this study, both populations of small spindle cells as well as large spider shape cells demonstrated a robust If current typical current of HCN channel subtypes (FIG. 15, 16, 17).

The present invention is exemplified with respect to lentiviral vectors. However, this is exemplary only, and the invention can be broadly applied to include any means for activating the requisite genes in stem cells, such as ADSC. The following examples are intended to be illustrative only, and not unduly limit the scope of the appended claims.

The following references are incorporated by reference in their entirety for all purposes.

Arnolds, D. E., et al., TBX5 drives SSN5A expression to regulate cardiac conduction system function. J Clin Invest, 2012. 122(7): p. 2509-18.

Avci-Adali, M., et al., Optimized conditions for successful transfection of human endothelial cells with in vitro synthesized and modified mRNA for induction of protein expression. J Biol Eng, 2014. 8(1): p. 8.

Bai, X., et al., Tracking long-term survival of intramyocardially delivered human adipose tissue-derived stem cells using bioluminescence imaging. Mol Imaging Biol, 2011. 13(4): p. 633-45.

Bakker, M. L., et al., T-box transcription factor TBX3 reprogrammes mature cardiac myocytes into pacemaker-like cells. Cardiovasc Res, 2012. 94(3): p. 439-49.

Cho, H. C. and E. Marban, Biological therapies for cardiac arrhythmias: can genes and cells replace drugs and devices? Circ Res, 2010. 106(4): p. 674-85.

Diego S. D'Astolfo, D. S. et al., Efficient Intracellular Delivery of Native Proteins, CELL 2015. 161(3): 674-690.

DiFrancesco, D., et al., Properties of the hyperpolarizing-activated current (if) in cells isolated from the rabbit sino-atrial node. J Physiol, 1986. 377: p. 61-88.

Hashem, S. I., et al., SHOX2 regulates the pacemaker gene program in embryoid bodies. Stem Cells Dev, 2013. 22(21): p. 2915-26.

Hatcher, C. J. and C. T. Basson, Specification of the cardiac conduction system by transcription factors. Circ Res, 2009. 105(7): p. 620-30.

Hoogaars, W. M., et al., TBX3 controls the sinoatrial node gene program and imposes pacemaker function on the atria. Genes Dev, 2007. 21(9): p. 1098-112.

Hu, Y. F., et al., Biological pacemaker created by minimally invasive somatic reprogramming in pigs with complete heart block. Sci Transl Med, 2014. 6(245): p. 245ra94.

Islas, J. F., et al., Transcription factors ETS2 and MESP1 transdifferentiate human dermal fibroblasts into cardiac progenitors. P.N.A.S. USA, 2012. 109(32): p. 13016-21.

Jung, J. J., et al., Programming and isolation of highly pure physiologically and pharmacologically functional sinus-nodal bodies from pluripotent stem cells. Stem Cell Reports, 2014. 2(5): p. 592-605.

Kapoor, N., et al., Direct conversion of quiescent cardiomyocytes to pacemaker cells by expression of TBX18. Nat Biotechnol, 2013. 31(1): p. 54-62.

Stankovicova, T., et al., Isolation and morphology of single Purkinje cells from the porcine heart. Gen Physiol Biophys, 2003. 22(3): p. 329-40.

White, S. M. and W. C. Claycomb, Embryonic stem cells form an organized, functional cardiac conduction system in vitro. Am J Physiol Heart Circ Physiol, 2005. 288(2): p. H670-9.

All UniProt cites herein are incorporated by reference herein, including the sequences linked thereto, in their entirety for all purposes.

The invention claimed is:

1. A method of treating an arrhythmia, comprising
   a) obtaining adult tissue-derived stem cells from a patient with an arrhythmic heart;
   b) inducing lineage commitment of said adult tissue-derived stem cells towards Purkinje and pacemaker cardiomyocyte cells through sequential epigenetic reprogramming by sequentially expressing SHOX2 before TBX5 before HCN2 ("SHOX2>TBX5>HCN2"), and
   c) introducing said Purkinje cells or said pacemaker cells, or both, into said arrhythmic heart.

2. The method of claim 1, wherein the adult tissue-derived stem cells are uncultured prior to the inducing step b).

3. The method of claim 1, wherein both said pacemaker cells and said Purkinje cells are used together to reconstitute a damaged sinus node of said patient.

* * * * *

SEQUENCE LISTING

```
<160> NUMBER OF SEQ ID NOS: 21

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
gagggaaacg cttatgggag c                                      21

<210> SEQ ID NO 2
<211> LENGTH: 22
<212> TYPE: DNA
<213> ORGANISM: Artificial Sequence
<220> FEATURE:
<223> OTHER INFORMATION: Primer
```

```
<400> SEQUENCE: 2
cgccgtctaa gttctccaaa tc                                          22

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
tcagcgactc ggattttaag ga                                          22

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
ggaggcggcg aatggataa                                              19

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
acattggtac tgagtgcatg aac                                         23

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
gccatcctct atccttcctg g                                           21

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
tccctcgaaa ctaacaactt ccg                                         23

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
tctgctccct atgcttctct c                                           21

<210> SEQ ID NO 9
<211> LENGTH: 21
```

```
<212> TYPE: DNA
<213> ORGANISM: Artificial Sequence
<220> FEATURE:
<223> OTHER INFORMATION: Primer

<400> SEQUENCE: 9
ccaaggcaca tatccactgc t                                              21

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
gtctcgatca cgtagaagac ct                                             22

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
catgccaccg ctttaatcca g                                              21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
attgtagcca ccagtttccg a                                              21

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
agcagtggaa atcgagcagg                                                20

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
ggtcccagta aaaccggaag t                                              21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
```

-continued

```
gaacaggaga gggtcaagtc g                                              21

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
cattgaagac aatccagggt gt                                             22

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
gccttcaata gattgtttcc cct                                            23

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
ctcgggcctg tagaaccat                                                 19

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tggagtcagc ggtttctgtc                                                20

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
ttgtgtcttc tggtgctctc t                                              21

<210> SEQ ID NO 21
<211> LENGTH: 68
<212> TYPE: DNA
<213> ORGANISM: Artificial Sequence
<220> FEATURE:
<223> OTHER INFORMATION: Artificial plasmid

<400> SEQUENCE: 21
ctggatcccc gatctcgagc tcaagcttcg aattctgcag tcgacggtac cgcgggcccg    60
ggatccgc                                                             68
```